United States Patent
Verespej et al.

(10) Patent No.: US 9,248,242 B2
(45) Date of Patent: Feb. 2, 2016

(54) ANTI-NEEDLE STICK SAFETY DEVICE FOR INJECTION DEVICE

(71) Applicant: Safety Syringes, Inc., Carlsbad, CA (US)

(72) Inventors: James M. Verespej, San Marcos, CA (US); Ryan Schoonmaker, San Marcos, CA (US); Philip Dowds, San Diego, CA (US); Frederic P. Field, San Diego, CA (US)

(73) Assignee: SAFETY SYRINGES, INC., Carlsbad, CA (US)

( * ) Notice: Subject to any disclaimer, the term of this patent is extended or adjusted under 35 U.S.C. 154(b) by 125 days.

(21) Appl. No.: 13/800,415

(22) Filed: Mar. 13, 2013

(65) Prior Publication Data

US 2014/0039406 A1    Feb. 6, 2014

Related U.S. Application Data

(60) Provisional application No. 61/732,846, filed on Dec. 3, 2012, provisional application No. 61/636,526, filed on Apr. 20, 2012.

(51) Int. Cl.
*A61M 5/32* (2006.01)
*A61M 5/24* (2006.01)
*A61M 5/28* (2006.01)

(52) U.S. Cl.
CPC .............. *A61M 5/3202* (2013.01); *A61M 5/24* (2013.01); *A61M 5/28* (2013.01); *A61M 5/326* (2013.01); *A61M 2005/2433* (2013.01); *A61M 2005/3261* (2013.01); *A61M 2005/3264* (2013.01)

(58) Field of Classification Search
USPC .................. 128/919; 604/110, 192, 198, 263
See application file for complete search history.

(56) References Cited

U.S. PATENT DOCUMENTS

| | | | | |
|---|---|---|---|---|
| 5,425,531 | A | * 6/1995 | Perrault | 267/180 |
| 5,562,626 | A | * 10/1996 | Sanpietro | 604/110 |
| 6,416,323 | B1 | * 7/2002 | Grenfell et al. | 433/90 |

(Continued)

FOREIGN PATENT DOCUMENTS

| | | |
|---|---|---|
| FR | 2860162 | 4/2005 |
| FR | 2971424 | 8/2012 |

(Continued)

OTHER PUBLICATIONS

WO, PCT/US2013/037476 ISR, Aug. 6, 2013.

*Primary Examiner* — Nicholas Lucchesi
*Assistant Examiner* — Gerald Landry, II
(74) *Attorney, Agent, or Firm* — One LLP

(57) ABSTRACT

A safety device for a medicine cartridge comprising a body for receiving a cartridge, a guard for covering a used needle, a plunger to dispense medicine from the cartridge and a spring for activation of the guard. The trigger fingers of the guard are spaced to avoid or minimize contact with the spring flange during assembly to avoid trigger finger unseating. An elongated trigger finger head enables the device to activate for all known syringe and syringe plunger tolerances. The spring end coils have larger diameter than the inner coils to reduce the likelihood of the spring end coil end interfering with the cartridge subassembly. Syringe capture features are configured to retain a syringe having a small round or conventional cut flange in place during use and reduce the stress on the syringe flange during insertion while maintaining the ability to hold the syringe in place during use.

23 Claims, 35 Drawing Sheets

(56) References Cited

U.S. PATENT DOCUMENTS

| | | | |
|---|---|---|---|
| 6,716,191 B2* | 4/2004 | Sergio | 604/110 |
| 6,872,190 B1* | 3/2005 | Denis et al. | 604/110 |
| 6,939,330 B1* | 9/2005 | McConnell-Montalvo et al. | 604/197 |
| 2003/0212370 A1* | 11/2003 | Barrelle | 604/198 |
| 2005/0277894 A1* | 12/2005 | Westbye et al. | 604/198 |
| 2006/0036217 A1 | 2/2006 | Doyle | |
| 2007/0239117 A1 | 10/2007 | Chelak et al. | |
| 2008/0208140 A1* | 8/2008 | Barrelle | 604/198 |
| 2008/0300549 A1* | 12/2008 | Verespej et al. | 604/198 |
| 2009/0209939 A1 | 8/2009 | Verespej et al. | |
| 2009/0270803 A1* | 10/2009 | Brunel | 604/110 |
| 2010/0211017 A1* | 8/2010 | Chevallier et al. | 604/197 |
| 2010/0217204 A1* | 8/2010 | Field et al. | 604/198 |
| 2013/0184655 A1 | 7/2013 | Lanzi et al. | |
| 2014/0163476 A1* | 6/2014 | Chevallier et al. | 604/198 |

FOREIGN PATENT DOCUMENTS

| | | |
|---|---|---|
| WO | WO 01/41841 | 6/2001 |
| WO | WO 01/85239 | 11/2001 |
| WO | WO 2011/157930 | 12/2011 |
| WO | WO 2012/110715 | 8/2012 |
| WO | WO 2012/138318 | 10/2012 |

* cited by examiner

ANTI-NEEDLE STICK SAFETY DEVICE FOR INJECTION DEVICE

CROSS-REFERENCE TO RELATED APPLICATIONS

This application claims the benefit of U.S. Provisional Application No. 61/732,846, filed Dec. 3, 2012, and U.S. Provisional Application No. 61/636,526, filed Apr. 20, 2012, which applications are incorporated herein by reference.

FIELD

The embodiments provided herein relate generally to anti-needle stick safety systems for injection devices such as medicine cartridges, syringes and the like, and more particularly to a needle guard for an injection device such as a medicine cartridge, a syringe and the like, that includes a passively activated shield for covering a needle of the injection device.

BACKGROUND INFORMATION

Medication is often dispensed using a medicine cartridge, such as a glass syringe, having a barrel with a needle at one end and a plunger slidably inserted into the other end and coupled to a rubber stopper. Such cartridges are often referred to as "pre-filled syringes" because they may contain a specific dosage or volume medication when they are initially provided, as compared to conventional syringes that are furnished empty and filled by the user before making an injection.

The glass syringe and rubber stopper have, for years, provided an ideal drug storage closure having unique properties of impermeability to oxygen, low extractables, biocompatibility, durability, etc. However, they are both formed by processes that do not lend themselves to tight geometrical tolerances. Tight tolerances were not originally needed by these devices because they were not used mechanically with other devices.

Due to the risk of communicable diseases, a number of syringes and adapters have been developed that are intended to prevent accidental needle sticks and/or inadvertent reuse of a syringe. Conventional passive anti-needle stick safety devices for prefilled syringes must mount to the syringe but not interfere excessively with the force required to move the plunger rod during injection nor prevent the full travel of the plunger rod. The safety mechanism necessarily must be triggered toward the end of administration of the drug (near the end of the plunger rod travel).

In some instances of conventional devices, the distance between trigger fingers of such a safety device is less than the diameter of a standard medicine cartridge flange. Consequently, during insertion of the medicine cartridge subassembly into the safety device, the trigger fingers must be flexed outwardly, which causes unseating of the trigger fingers from the body of the safety device for a time until the medicine cartridge is sufficiently inserted into the safety device. This can lead to a partially activated device, which is described as one trigger finger seated and one trigger finger unseated. Furthermore, a serious problem with specific safety devices is the significant force required to insert the medicine cartridge into the safety device. The significant force puts a large amount of stress on the medicine cartridge flange, typically made of brittle material, which greatly increases the risk of breakage.

Prefilled single-dose glass syringes were originally designed to be used as a manually operated device. To facilitate this, a finger flange is typically formed at the proximal end of the syringe barrel by heating the glass and splaying the cylinder walls externally to form a flange. Two opposite sections of the resultant round flange were sometimes cut when the glass was still molten so as to produce a flange with more diametrically opposed surfaces suitable for being grasped and supported by the user's first two fingers. These operations commonly impose internal stresses in the glass around the flange area.

In order for the syringe to be integrated with these safety devices, it must be installed and rigidly held in place by some feature so that the syringe can resist displacement during needle insertion and medication dispensing. The syringe finger flange is the usual feature with which the auxiliary devices grasp and hold the syringe in position, however this is also the feature that sustains internal stresses during the manufacturing operations. As a result, it is common for syringes to break during the assembly operations with auxiliary devices causing the spread of glass fragments into surrounding product and machinery. This in turn causes assembly line stoppage, cleanup efforts, and line clearance (waste) or re-inspection of product. This problem has recently prompted syringe manufacturers to develop syringes with smaller round flanges (e.g. smaller overall diameter) so that the glass manufacturing methods impose fewer internal stresses. Additionally, the smaller exposed geometry of these flanges prevents the auxiliary devices from imposing large stresses to the flange during assembly and functional use.

However, these smaller flanges present less geometry with which the auxiliary devices can hold the syringe. Since most auxiliary devices are made of plastic using an injection molding process, the holding means for the syringe are commonly flexible elements that are integral to a main component of the device This avoids using a secondary component to secure the syringe, which would require additional manufacturing steps. As the syringe is inserted, these flexible elements displace away from the flange under the force of insertion, allowing the syringe to move up to a reference surface. Once the flange has reached the reference surface, the flexible elements substantially return to their previous position and thereby provide a force-limited retention of the syringe to the device. Because large auxiliary devices are not desirable, the flexible elements are usually small, which inherently limits how much they can elastically flex. Because the edge of the flange is round due to the molten state of the glass, etc. during forming, a large portion of the projected geometry with the small flange is not suitable for resisting an axial load on the syringe as would be generated in normal use of the device. Therefore, it is desirable to provide a means for increasing the holding strength of retention features for use with syringes having smaller flange diameters.

Accordingly, an improved needle guard for a medicine cartridge or syringe is desirable.

SUMMARY

The systems and methods described herein are directed to an anti needle stick safety device designed to be packaged around a medicine cartridge such as a prefilled syringe. The safety device is comprised of 4 parts which include: a body for receiving a medicine cartridge, a needle guard for covering a used needle, a plunger to dispense medicine from the medicine cartridge and a spring for activation of the needle guard. In the embodiments described herein, the trigger fingers are spaced apart such that the medicine cartridge flange will not come into contact with the trigger fingers during assembly, or in a worst case tolerance scenario, minimally contact the trigger fingers so that they do not unseat during assembly, consequently eliminating the risk of a partially activated device.

The current embodiments described herein contain four syringe capture features located on the body. Each syringe capture feature contains an angled surface which interfaces with the medicine cartridge flange during insertion. The result is a normal force, acting upon the angled surface, which has a force component in a direction directed away from the medicine cartridge flange forcing the syringe capture feature outward and allowing the medicine cartridge to be assembled with more ease, reducing the risk of medicine cartridge flange breakage.

In an alternative embodiment, the body including syringe retention features configured to retain a syringe having a small round flange in place during use and/or syringe retention features that reduce the stress on the syringe flange during insertion while maintaining the ability to hold the syringe in place during use.

In the embodiments described herein, the end coils of the spring, which can be described as the last several coils of the spring at both ends, have a larger diameter compared with the inner coils of the spring. This feature reduces the likelihood of a spring coil end to interfere with the medicine cartridge subassembly.

In the embodiments described herein, a novel elongated trigger finger head allows the device to activate for all known syringe and syringe plunger tolerances.

Other systems, methods, features and advantages of the invention will be or will become apparent to one with skill in the art upon examination of the following figures and detailed description.

DESCRIPTION OF THE DRAWINGS

The details of the embodiments provided herein, including fabrication, structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

DESCRIPTION OF EMBODIMENTS

Figure 1:
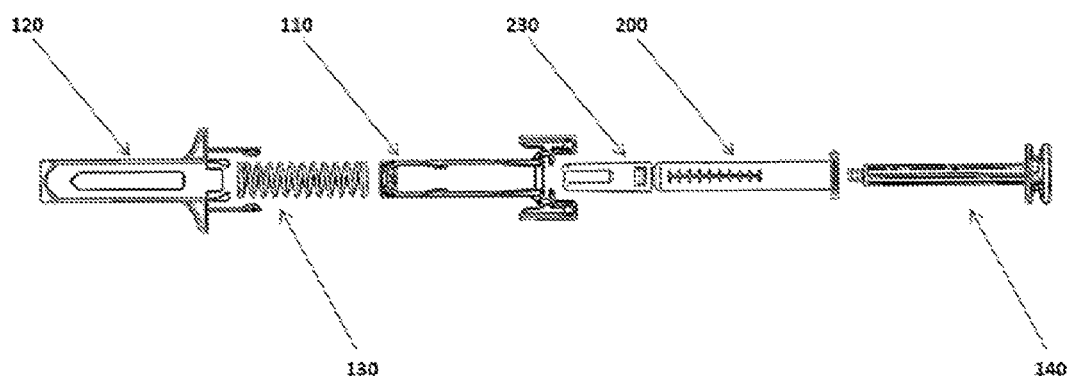
FIG. 1 is an exploded front view of a safety device with a medicine cartridge.

The embodiments described herein are directed to an anti needle stick safety device designed to be packaged around a medicine cartridge such as a prefilled syringe. The safety device 100 is comprised of 4 parts which include: a body 110 for receiving a medicine cartridge 200, a needle guard 120 for covering a used needle, a plunger 140 to dispense medicine from the medicine cartridge 200 and a spring 130 for activation of the needle guard 120 (FIG. 1).

Figure 2:
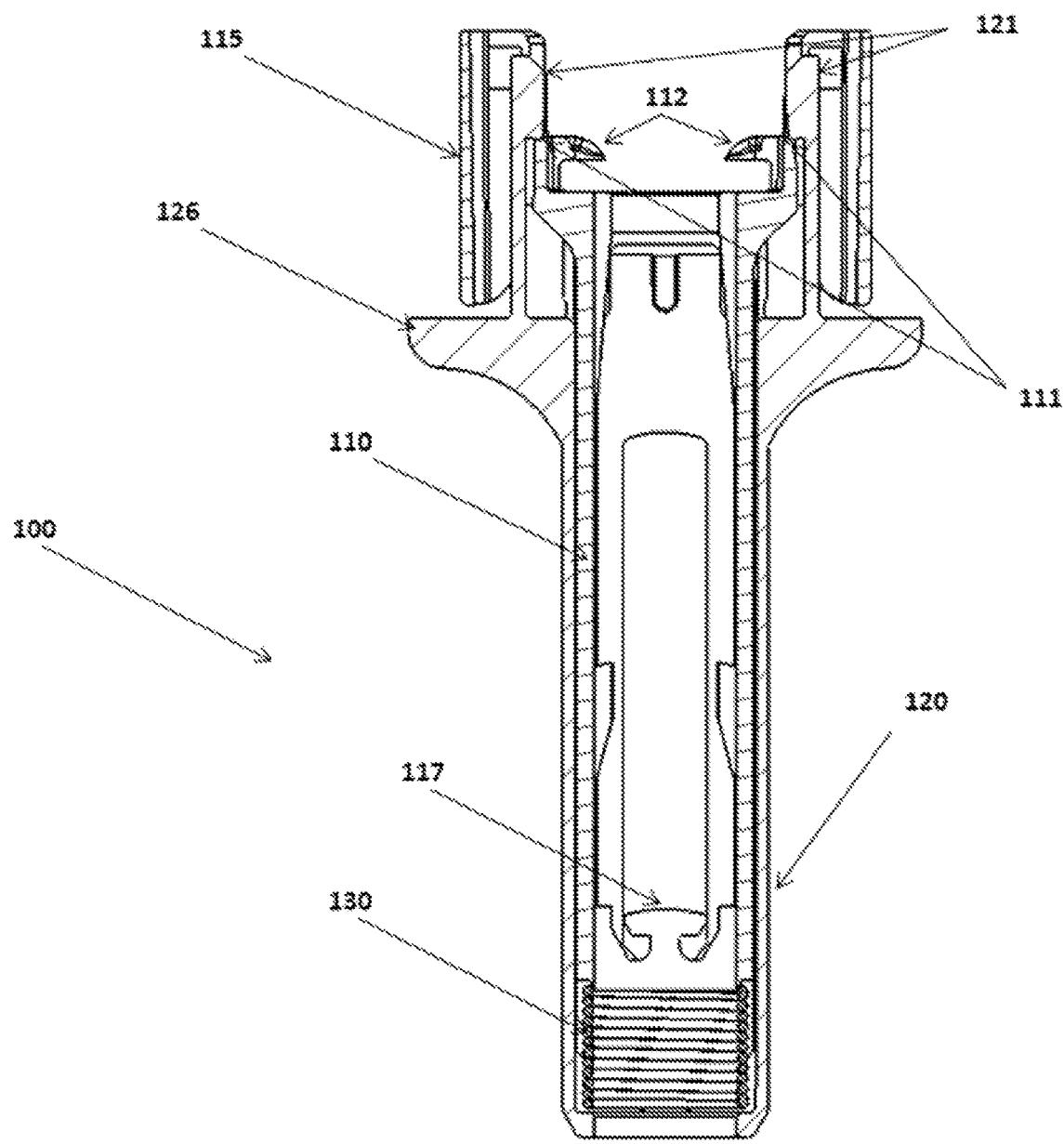
FIG. 2 is a cross sectional front view of the safety device.
Figure 3:
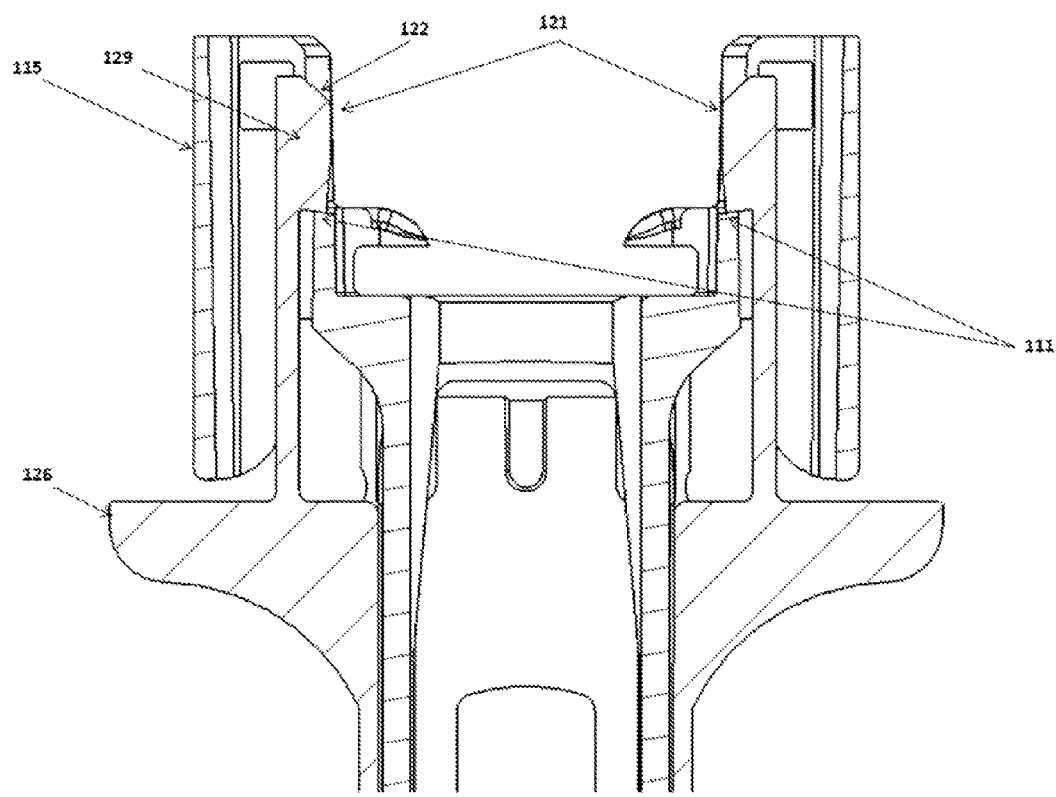
FIG. 3 is a cross sectional front detail view of the safety device enlarged in the device activation area.
Figure 4:
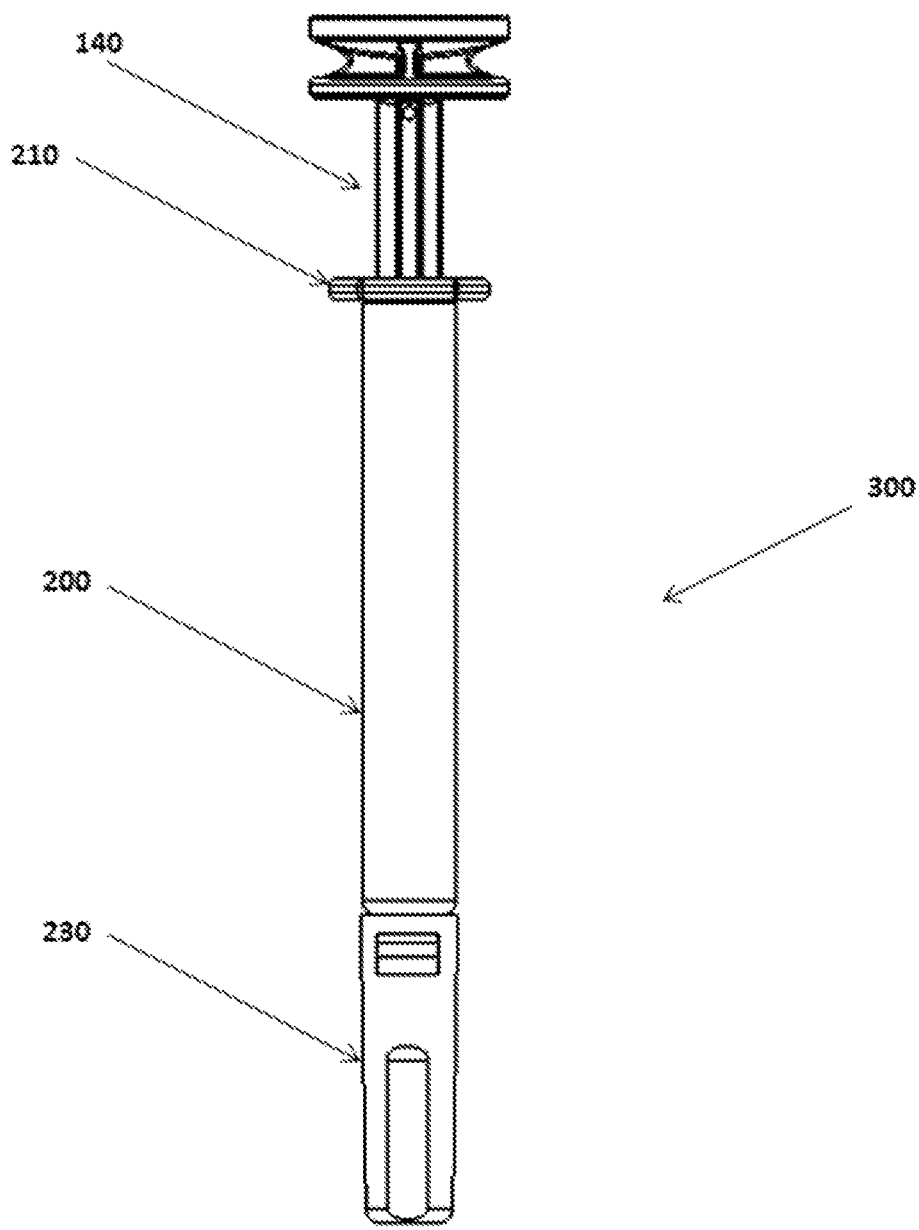
FIG. 4 is a front view of a medicine cartridge subassembly.

The safety device 100 comes packaged as shown in FIG. 2 with the spring 130 compressed by the body 110 and seated at the distal end of the needle guard 120. The guard 120 and body 110 are held together by two trigger fingers 121 extending from the needle guard which latch onto a body seat 111 on the body 110, coupling the body 110 and needle guard 120 under spring load, prior to device use (FIG. 2 and FIG. 3). Prior to assembling the medicine cartridge 200 to the safety device 100, a plunger 140 is coupled to the means of expelling the contents of the medicine cartridge 200. The plunger 140, and medicine cartridge 200 assembly 300 (FIG. 4), from here referred to as the medicine cartridge 300 subassembly, can then be assembled into the safety device 100.

Figure 5:
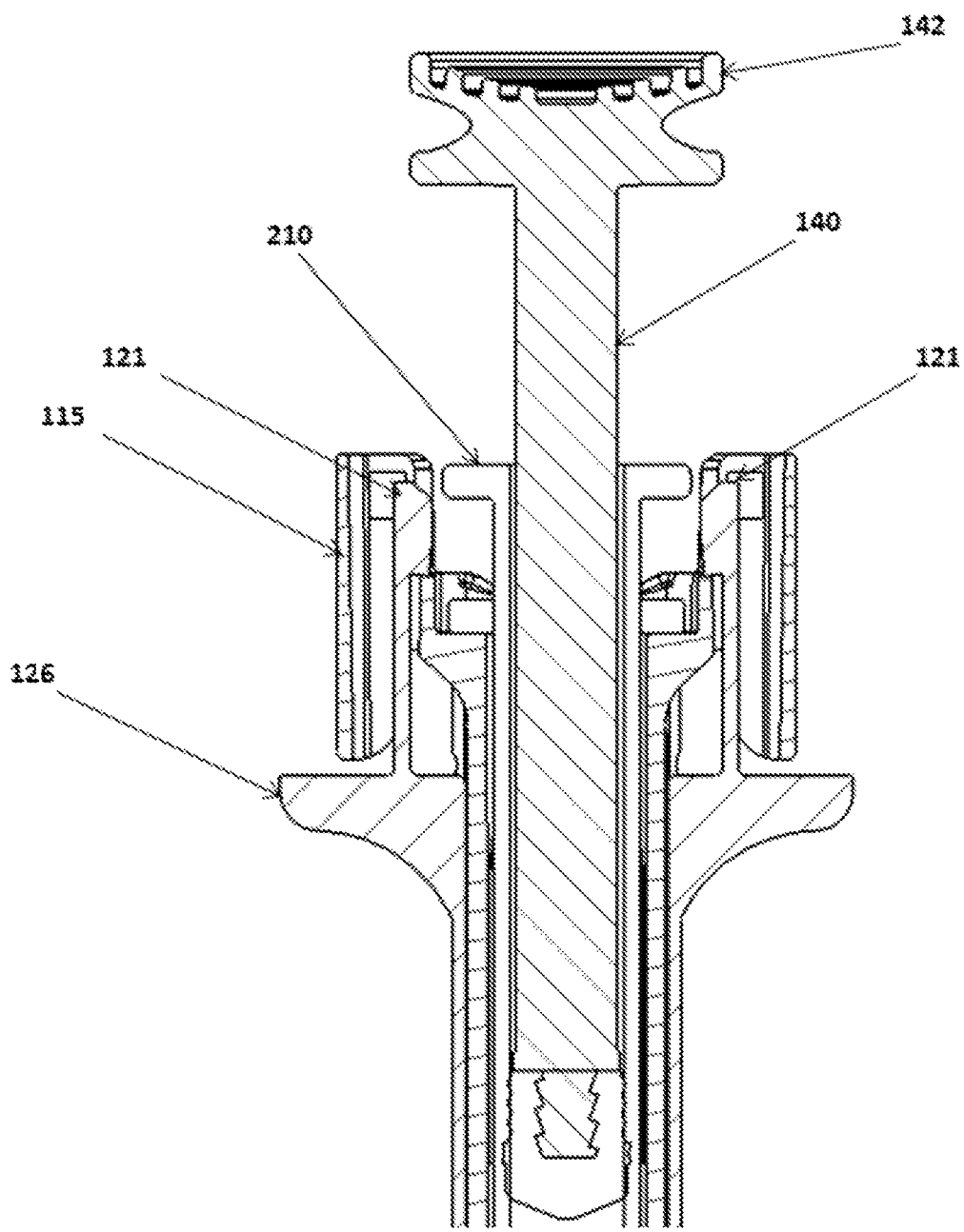
FIG. 5 is a cross sectional partial front view of the safety device with the medicine cartridge subassembly in the process of being inserted.

In some instances of the prior art, the distance between trigger fingers of such a safety device is less than the diameter of a standard medicine cartridge flange 210. Consequently, during insertion of the medicine cartridge subassembly 300 into the safety device 100 the trigger fingers 121 must flex, and unseat themselves from the body seat 111 for a time until the medicine cartridge subassembly 300 is sufficiently inserted into the safety device 100. This can lead to a partially activated device, which is described as one trigger finger seated and one trigger finger unseated. In the embodiments described here, the trigger fingers 121 are spaced such that the medicine cartridge flange 210 will not come into contact with the trigger fingers 121 during assembly (FIG. 5), or, in a worst case tolerance scenario, minimally contact the trigger fingers 121 so that they do not unseat themselves during assembly, consequently eliminating the risk of a partially activated device.

Figure 6:
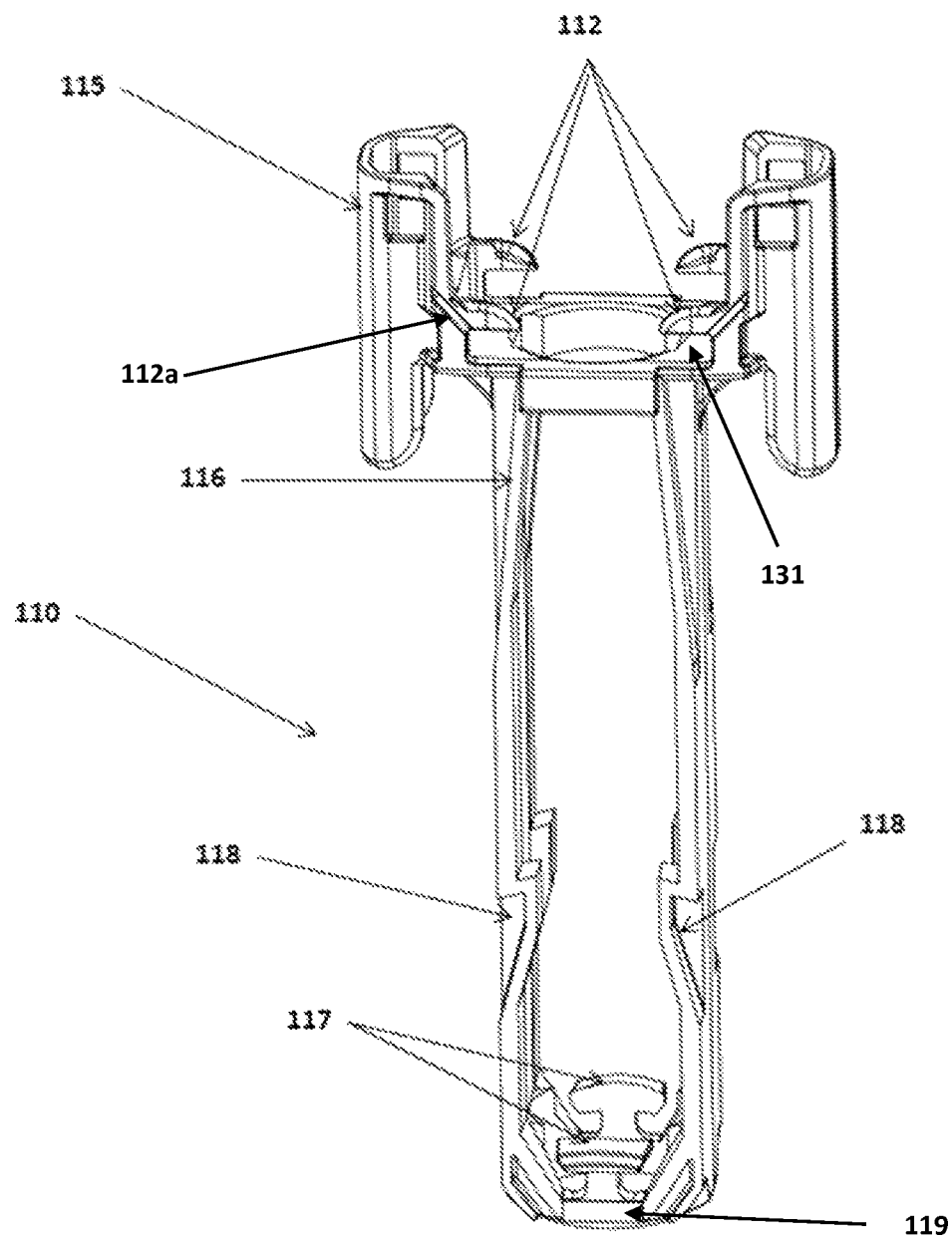
FIG. 6 is an isometric view of a body of the safety device.
Figure 7:
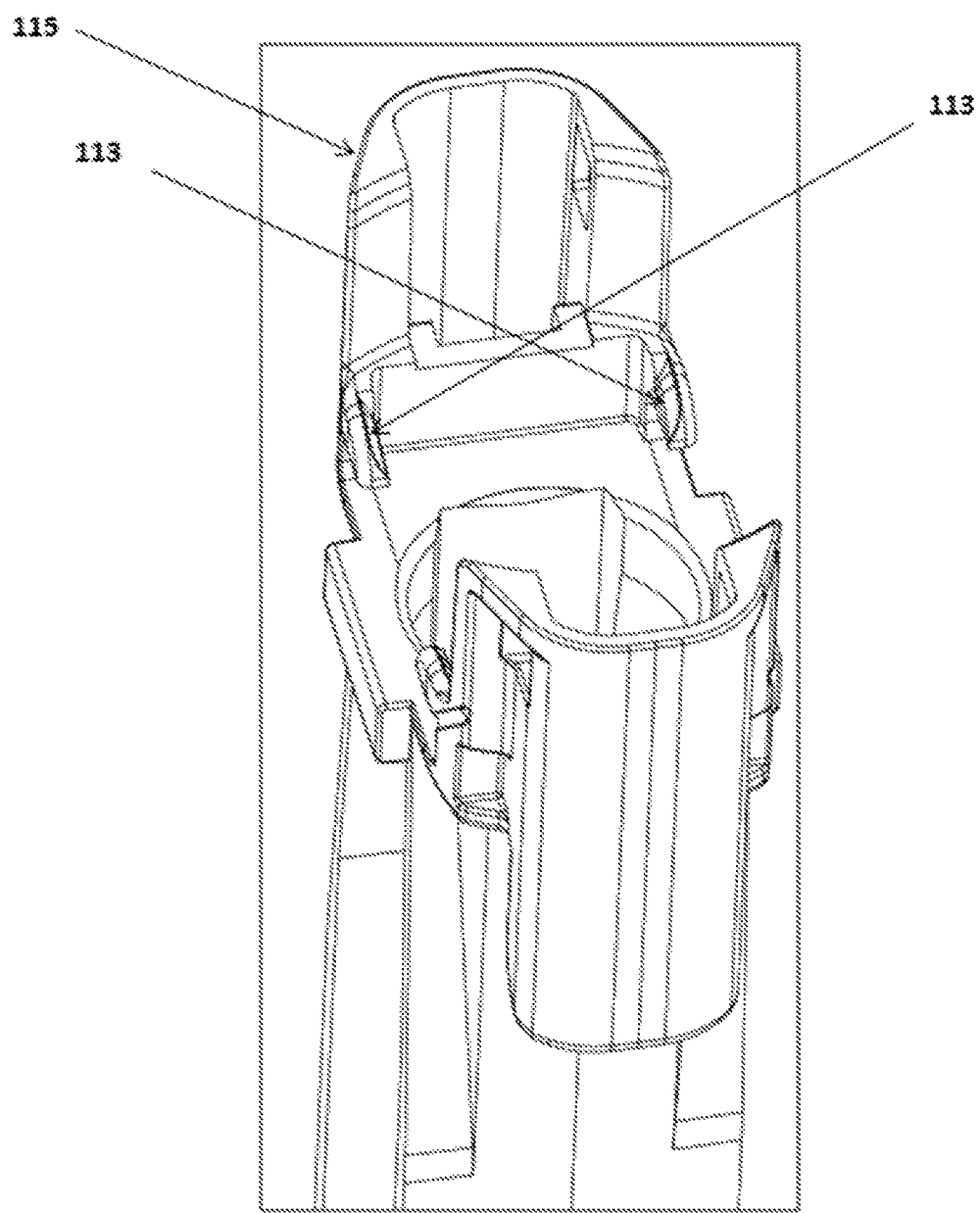
FIG. 7 is an isometric view of the body with particular emphasis on the syringe capture features, syringe capture feature chamfers and the trigger finger guards.
Figure 8B:
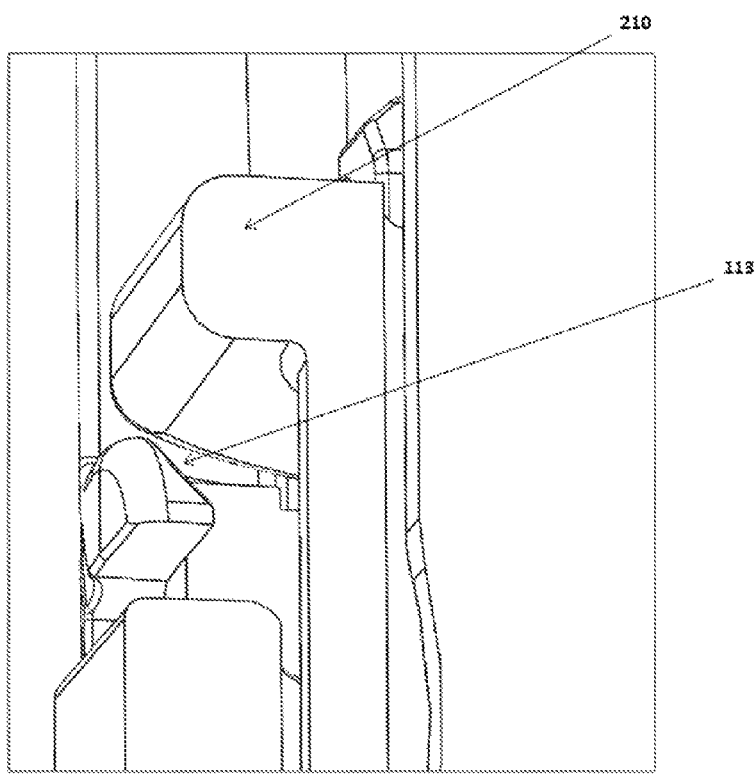
FIGS. 8A and B are enlarged partial isometric views of the medicine cartridge flange about to come into contact with the syringe capture features during medicine cartridge subassembly assembly.
Figure 8A:
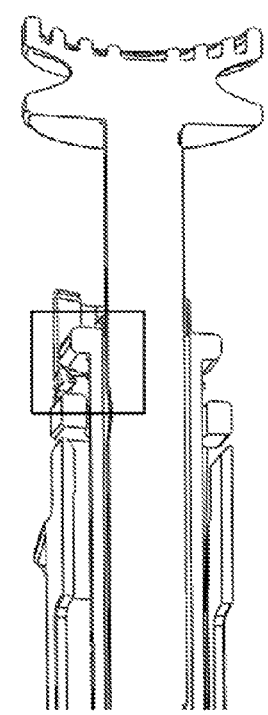

Furthermore, a serious problem with specific conventional safety devices is the significant force required to insert the medicine cartridge into the safety device. The significant force puts a large amount of stress on the medicine cartridge flange, typically made of brittle material, which greatly increases the risk of breakage. The current embodiments described here contain four syringe capture features 112 located on the body 110 extending upwardly a syringe flange reference surface 131 and then laterally inwardly from opposing ends of the syringe flange reference surface 131 in spaced relation with the syringe flange reference surface 131 (FIG. 6). Each syringe capture feature 112 contains an inwardly angled surface 113 which interfaces with the medicine cartridge flange 210 during insertion (FIGS. 7 and 8). The result is a normal force, acting upon the angled surface 113, which has a component in a direction away from the medicine cartridge flange 210 forcing the syringe capture feature 112 outward and allowing the medicine cartridge 200 to be assembled with more ease, reducing the risk of medicine cartridge flange 210 breakage.

Flexing grooves 112a in the lateral sides of the syringe retention features 112 are oriented substantially perpendicular to the direction of lateral deflection so that they may act as a hinge for the retention features 112 in the lateral direction, but at the same time providing rigidity to the retention features 112 in the distal, or more importantly, the proximal direction. The grooves 112a may also be angled as shown in FIG. 6, allowing the retention features 112 to flex proximally slightly (or less distally) during the initial lateral deflection to compensate for any distal deflection that they may experience as the medicine cartridge flange 210 is pushed proximally past them. If the retention features 112 were to flex too much distally, they might then occupy the space that was meant for the medicine cartridge flange 210 once it had reached the syringe reference surface 131, preventing the medicine cartridge 200 from being fully installed or captured by the retention features 112.

Figure 19:
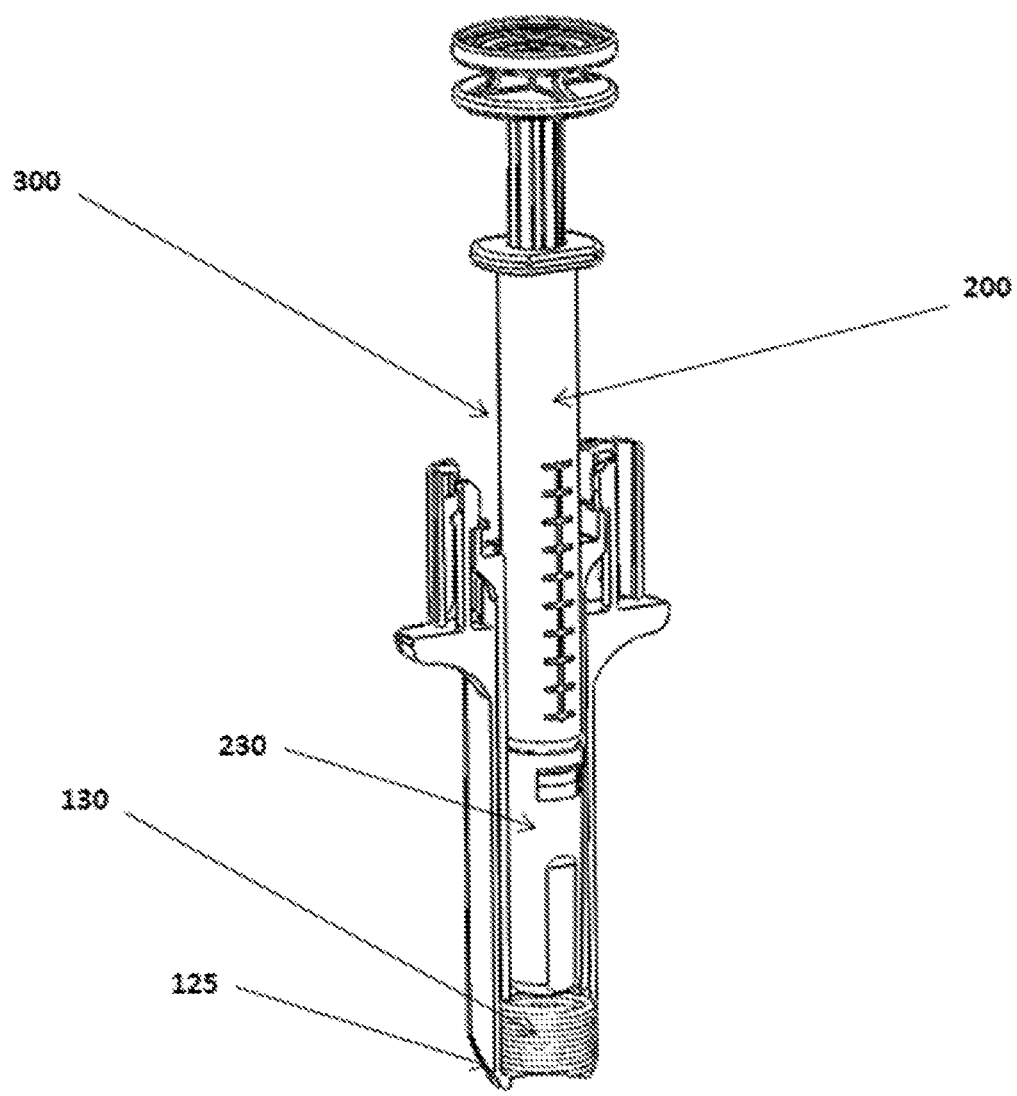
FIG. 19 is an isometric view of the safety device with a portion of the guard and body cut away to allow visualization of the medicine cartridge subassembly and the device spring as the medicine cartridge subassembly is being inserted into the safety device.
Figure 20:
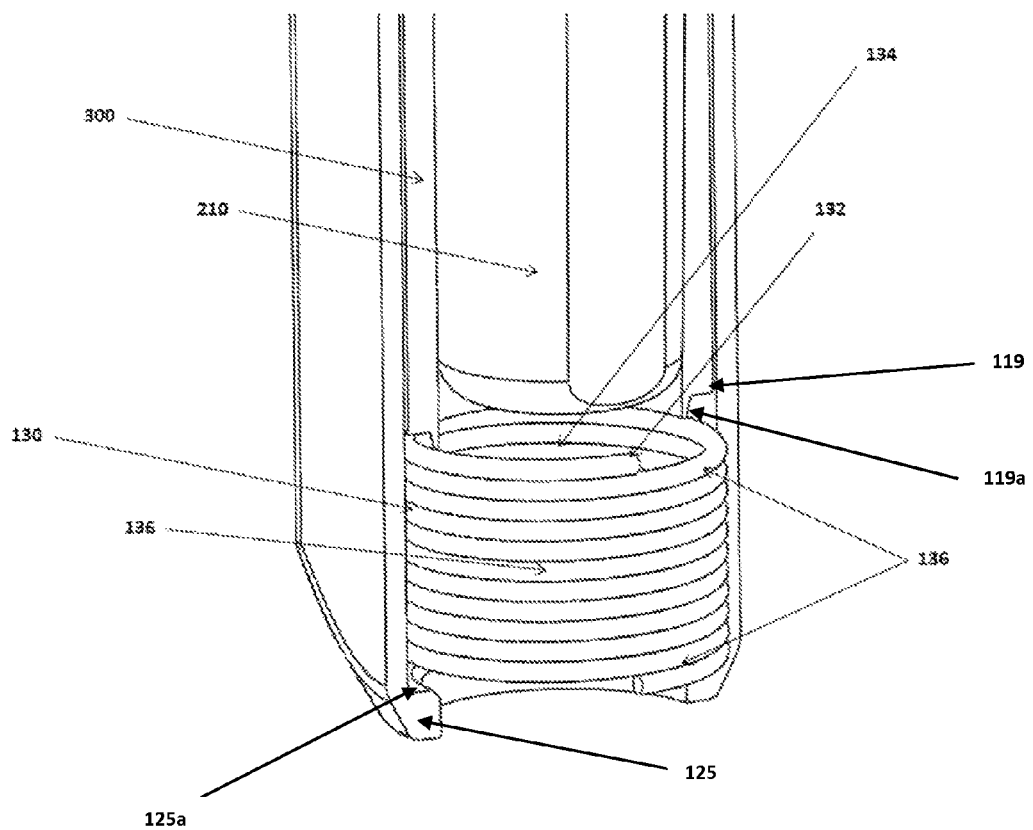
FIG. 20 is an enlarged partial isometric view of the safety device with a portion of the guard and body cut away to allow visualization of the medicine cartridge subassembly and the device spring as the medicine cartridge subassembly is being inserted into the safety device.
Figure 21:
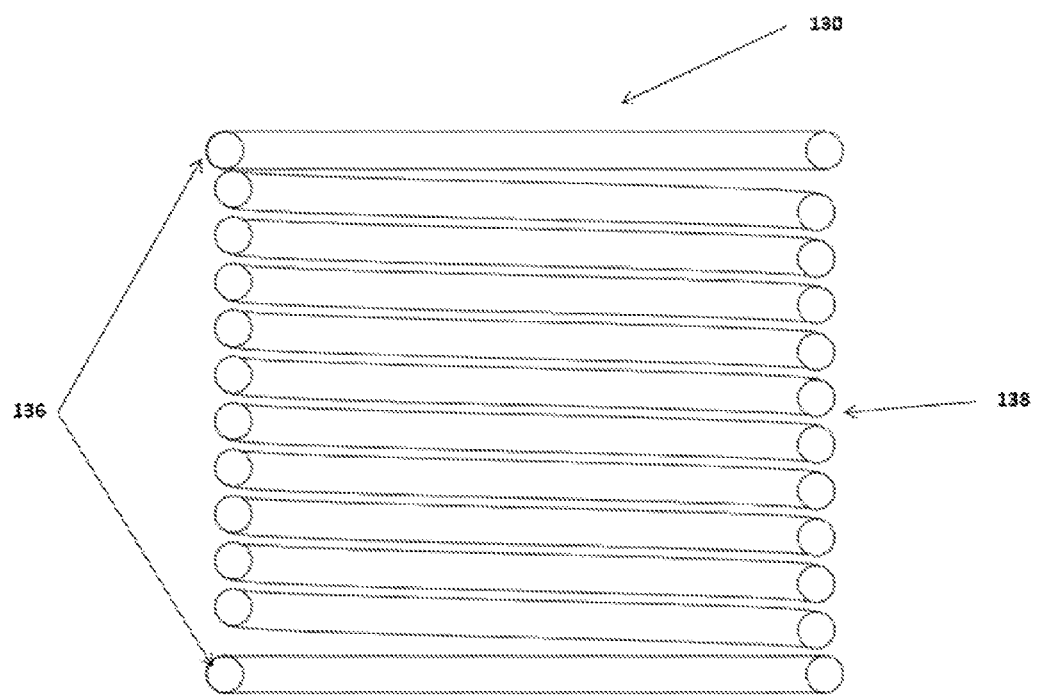
FIG. 21 is a cross sectional view of the spring.

Additionally, as the medicine cartridge subassembly 300 is inserted into the safety device 100 it must pass through the loaded spring 130 (FIGS. 19 and 20). In prior art designs, it is possible for the ends of the spring coil 132 to protrude into the inner diameter of the spring 134, which can interfere with the medicine cartridge subassembly 300 disallowing it to pass through the spring 130 and assemble properly. In the present design, the end coils 136 which can be described as the last several coils 136 of the spring 130 at both ends, are a larger diameter compared with the inner coils 138 of the spring (FIG. 21). This feature reduces the likelihood of a spring coil end 132 interfering with the medicine cartridge subassembly 300. A spring capture feature is provided in the form of an annular recess 119a formed in the distal end 119 of the body 110 and an inwardly projecting tab 125a forming as seat at the distal end 125 of the guard 120. The end coils 136 are captured in the recess 119a and are seated on tab 125.

Figure 9:
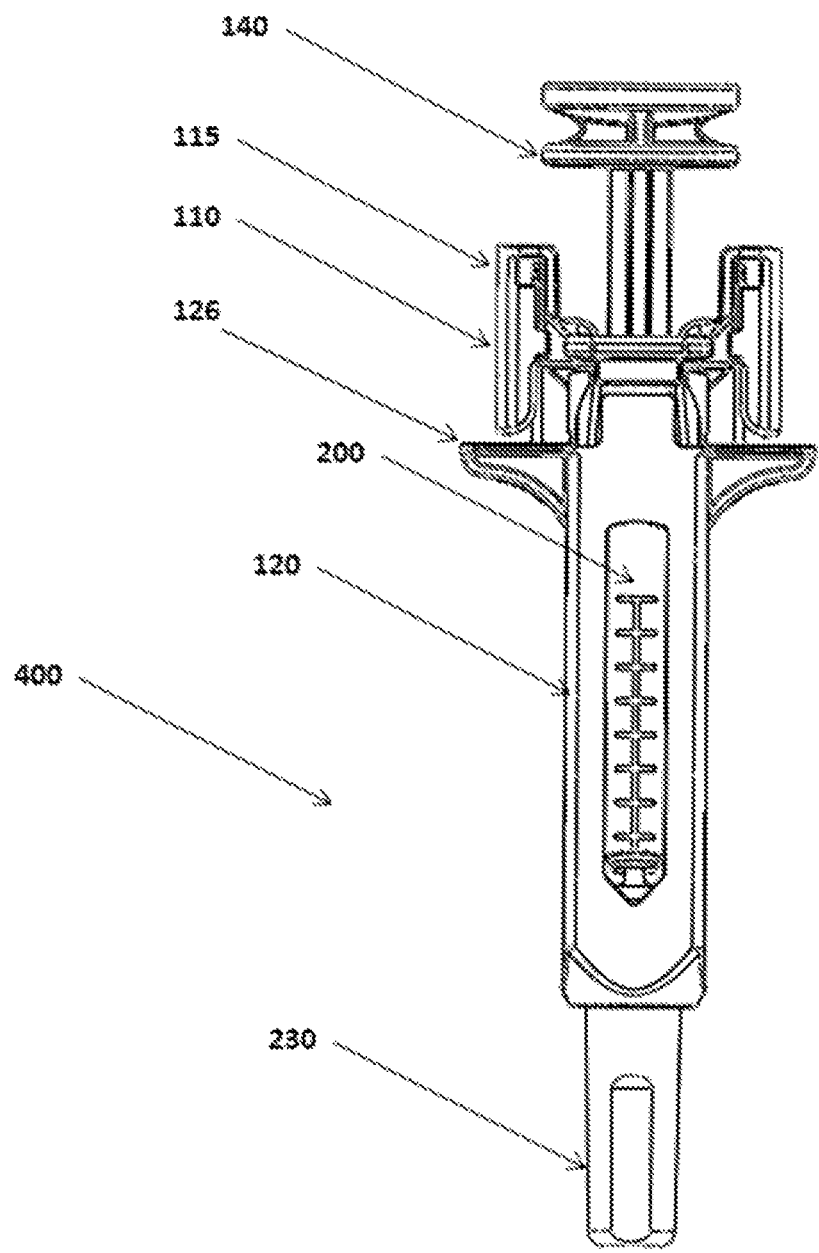
FIG. 9 is a front view of the safety device with the medicine cartridge subassembly fully assembled.
Figure 10:
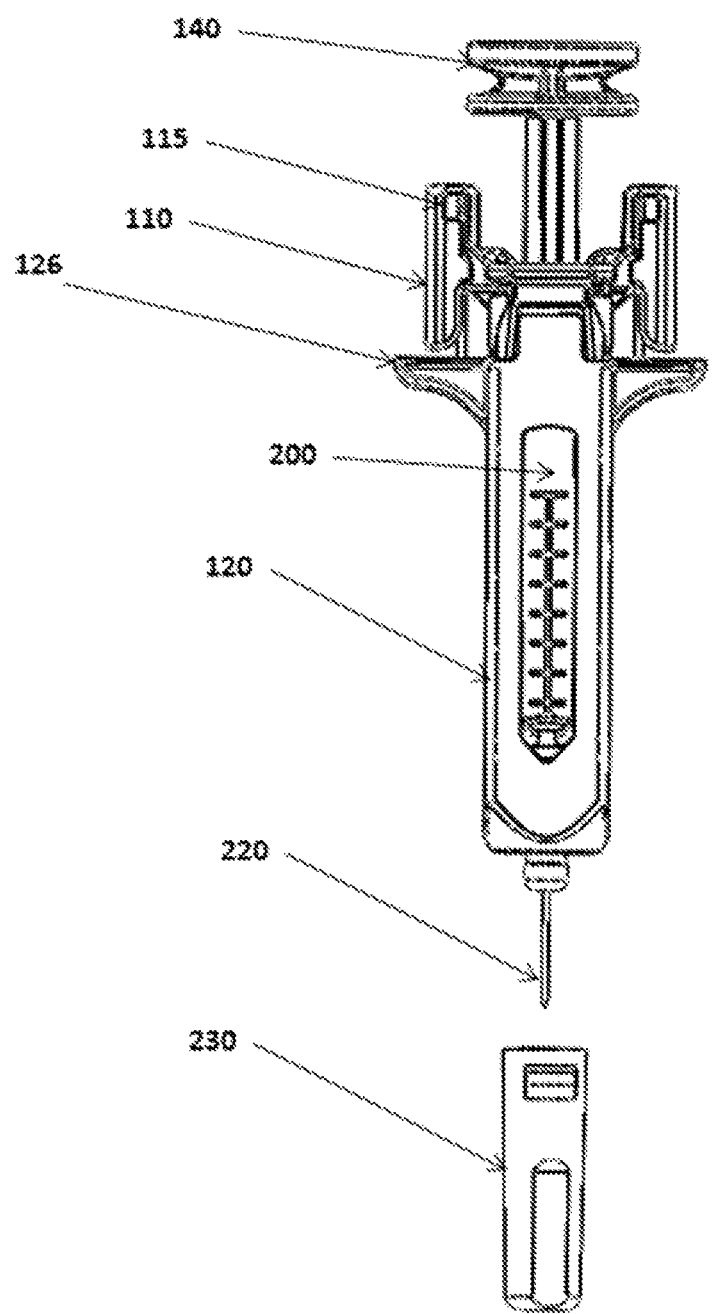
FIG. 10 is a front view of the safety device with the medicine cartridge subassembly fully assembled and the rigid needle shield removed.
Figure 11:
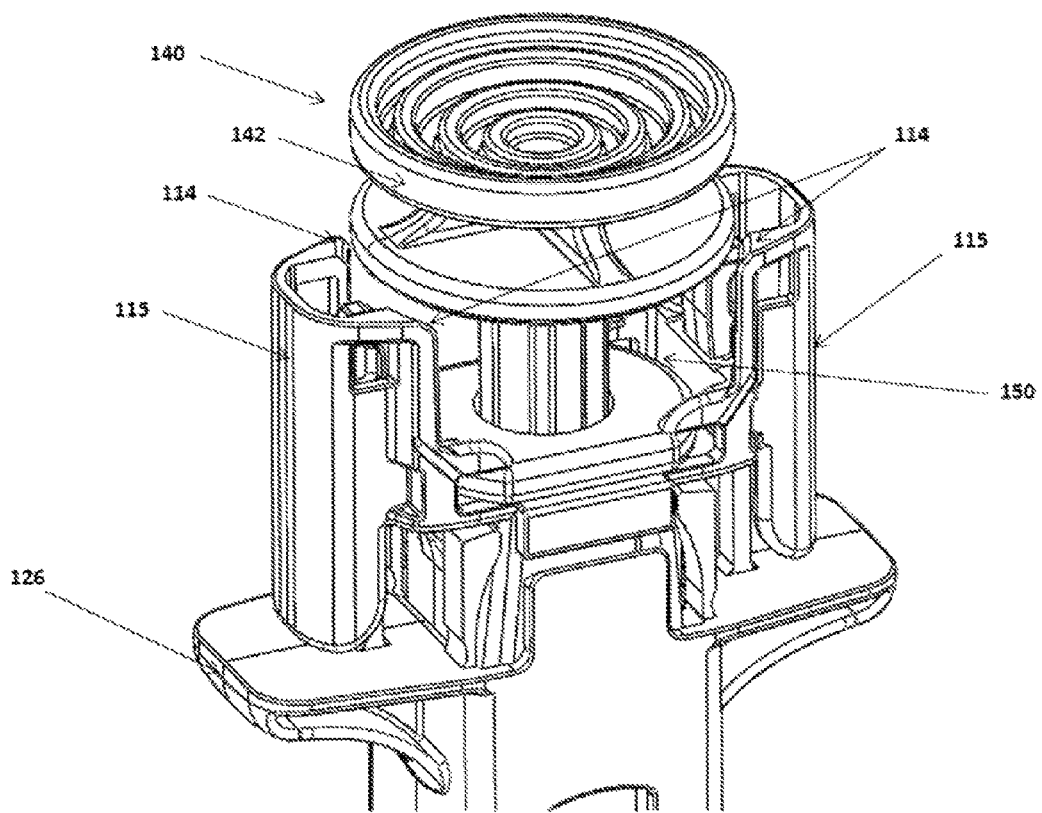
FIG. 11 is a partial isometric view of the safety device with the plunger head approaching the trigger finger guards during an injection.
Figure 12:
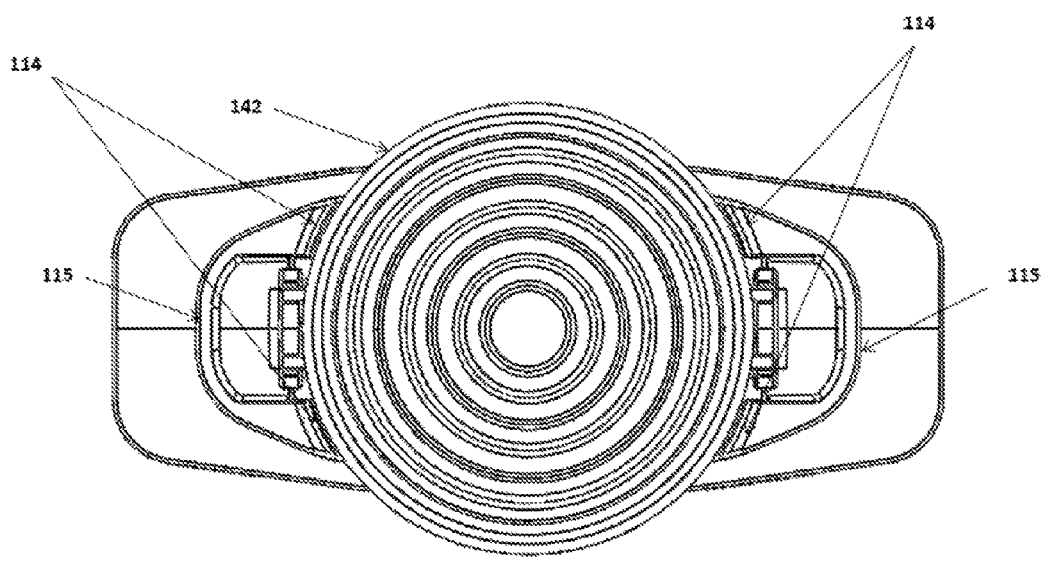
FIG. 12 is a top view of the safety device.
Figure 13:
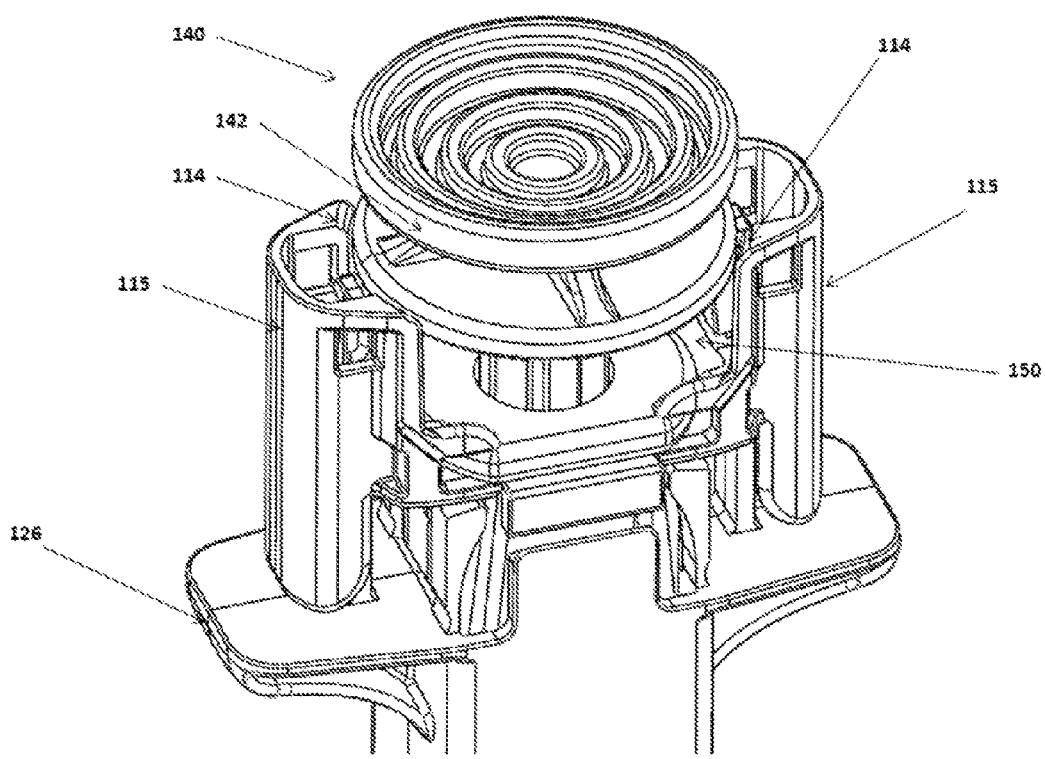
FIG. 13 is a partial isometric view of the safety device with the plunger head having entered the trigger finger guards during an injection.
Figure 14:
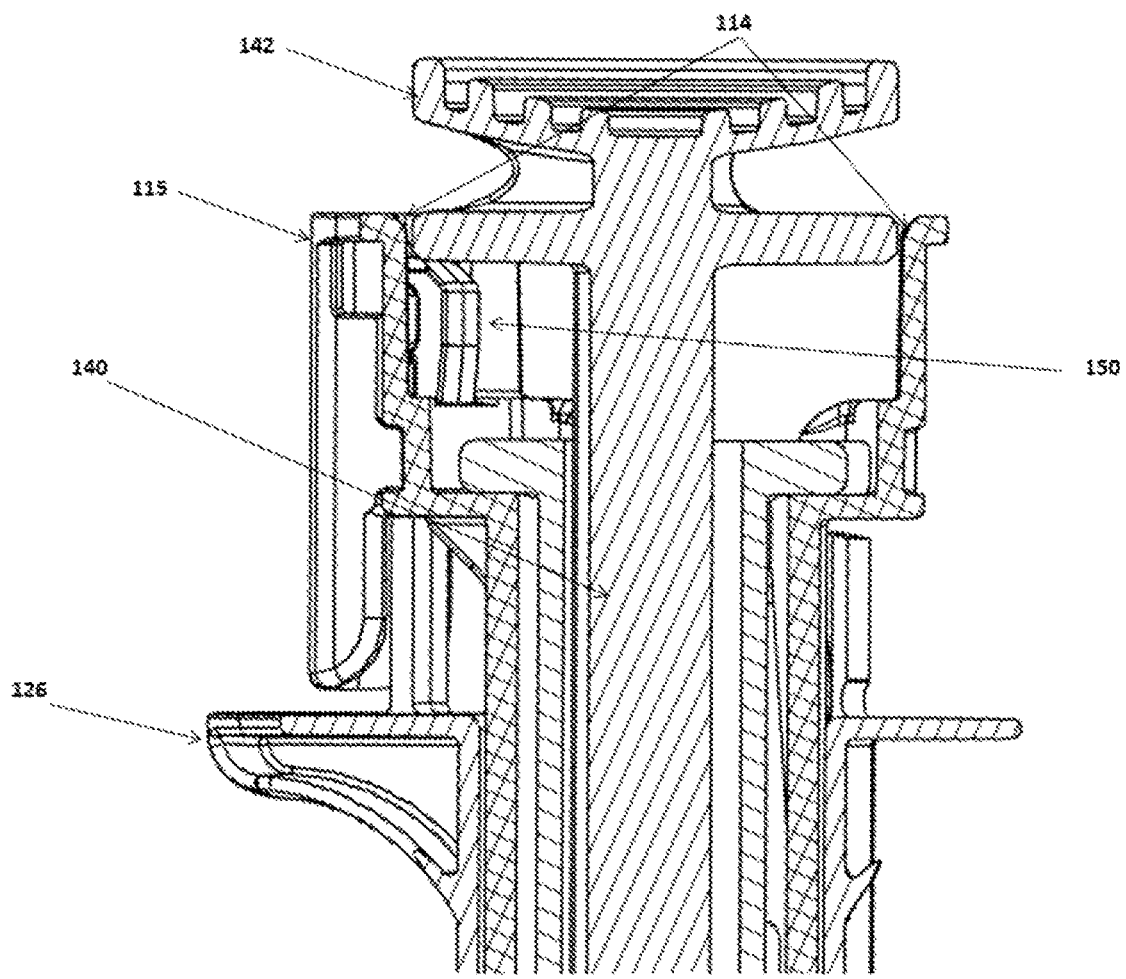
FIG. 14 is an angled partial cross sectional view of the safety device in a state where the plunger head is within the trigger finger guards, and about to come into contact with the trigger fingers during an injection.
Figure 15:
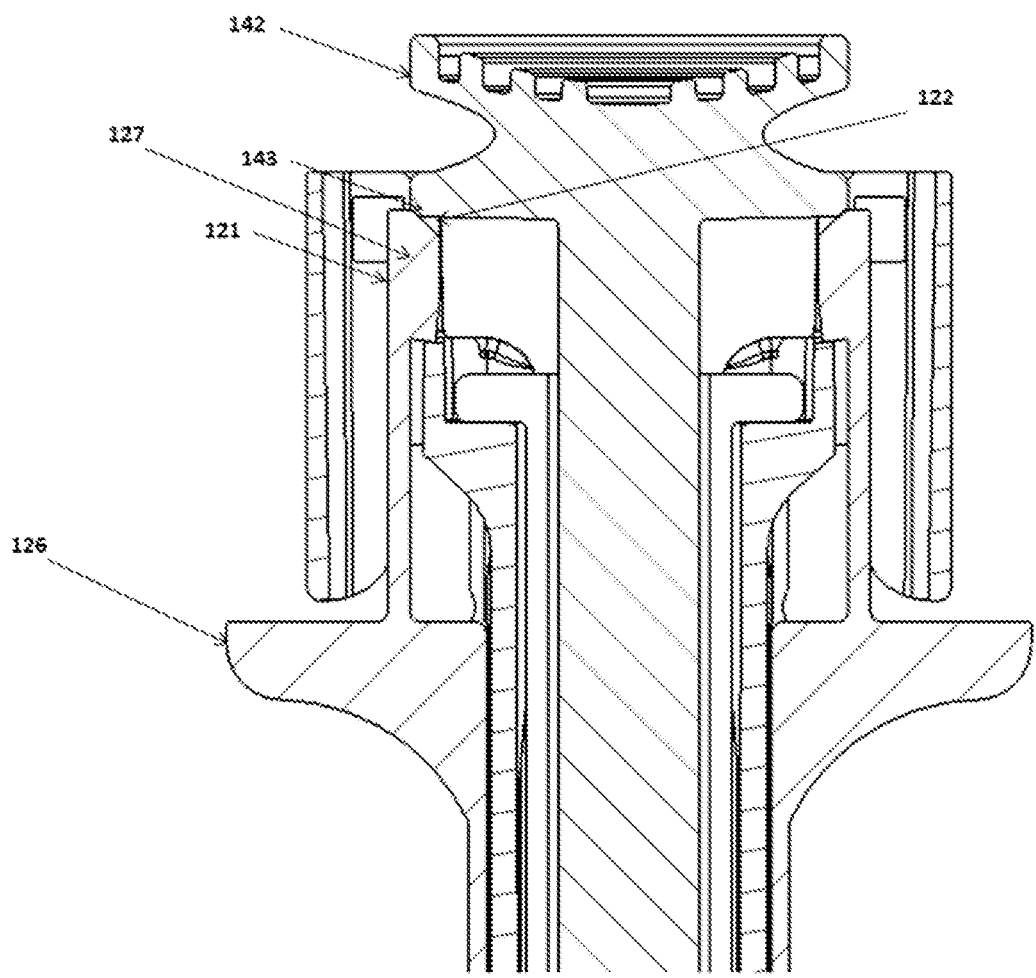
FIG. 15 is a partial cross sectional front view of the safety device when the plunger head is initially coming into contact with the trigger fingers during an injection.
Figure 16:
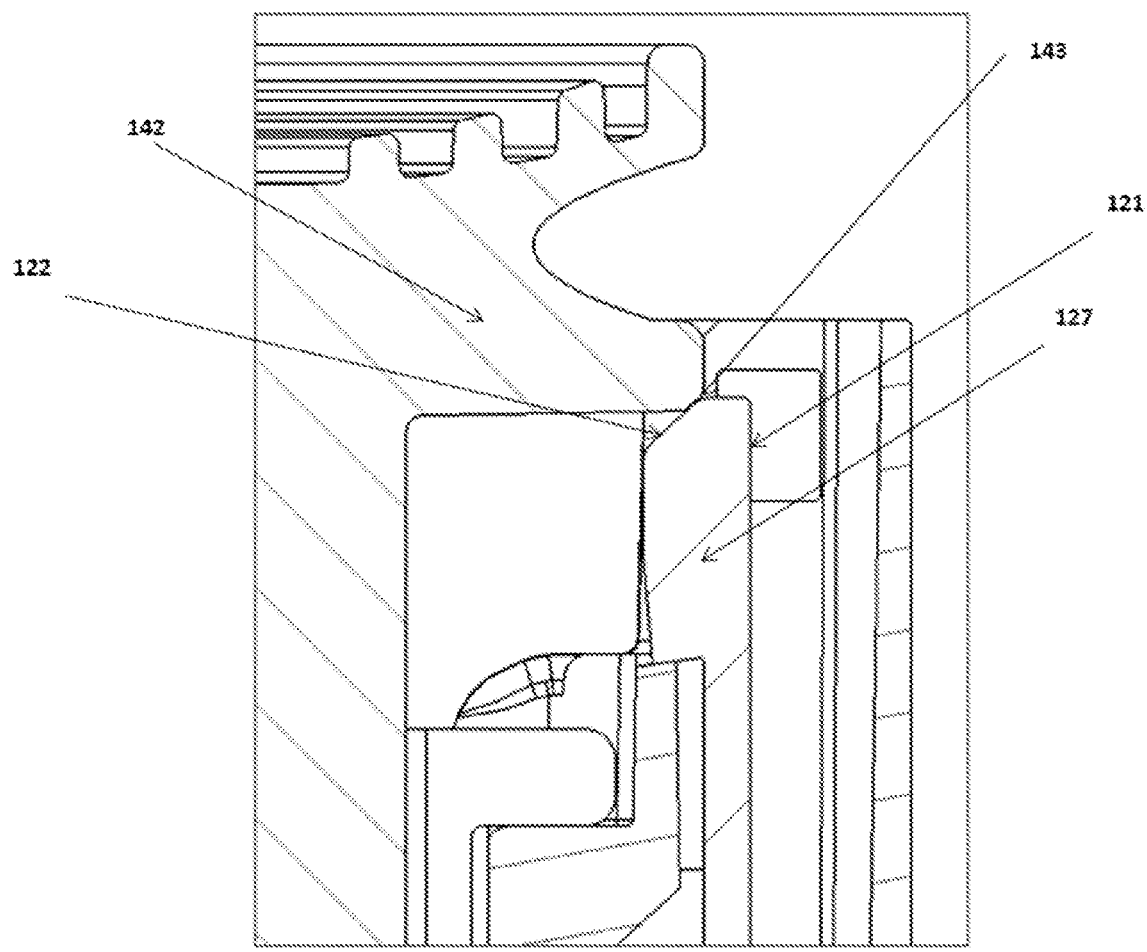
FIG. 16 is an enlarged partial cross sectional front view of the safety device when the plunger head is initially coming into contact with the trigger fingers during an injection.
Figure 17:
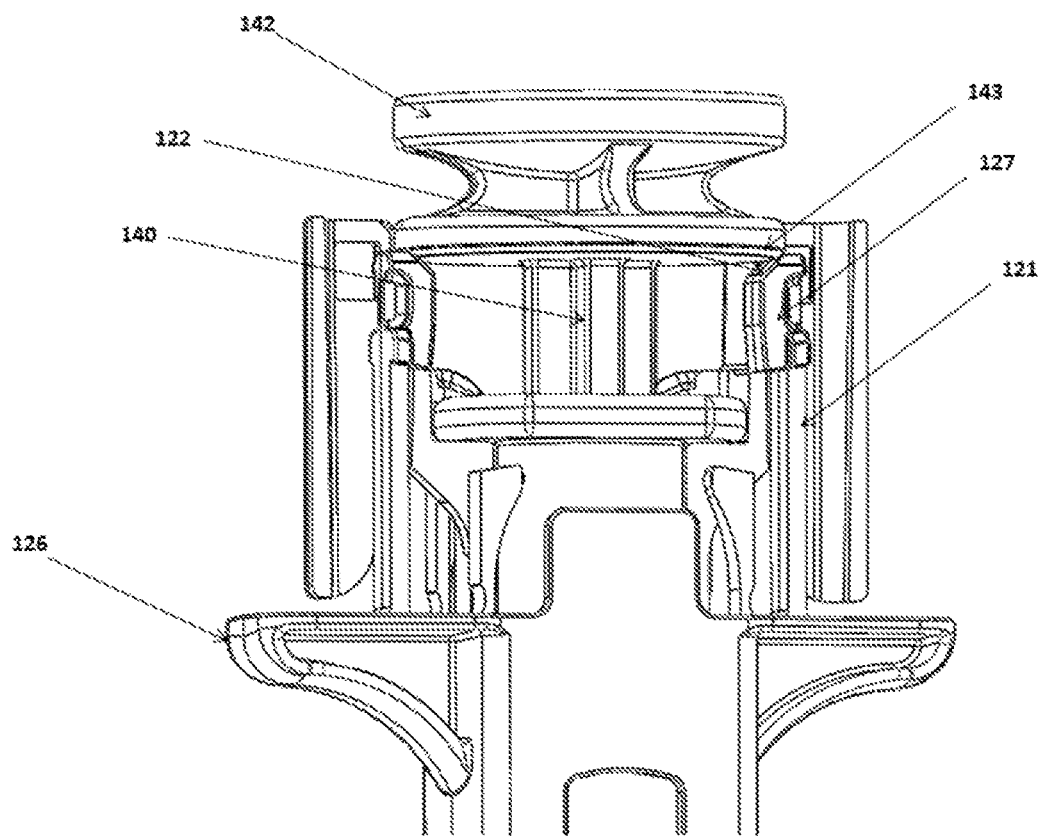
FIG. 17 is a partial isometric view of the safety device with a portion of the body cut away to allow visualization of the plunger head contacting the trigger fingers during an injection.
Figure 18:
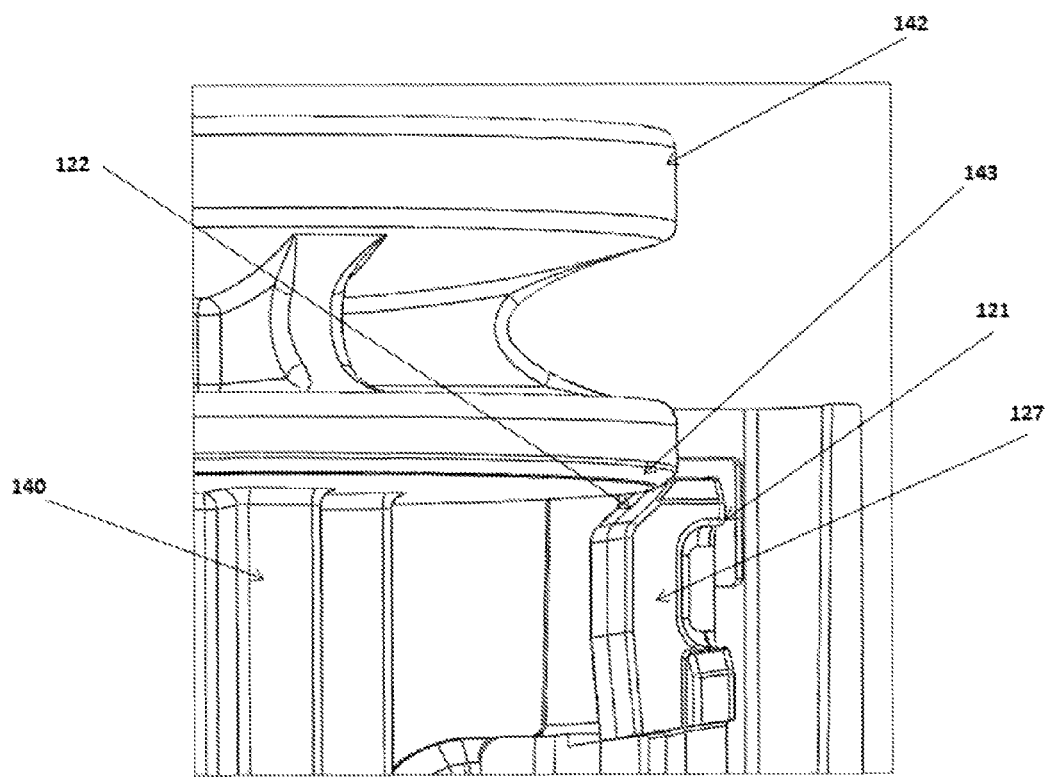
FIG. 18 is an enlarged partial isometric view of the safety device with a portion of the body cut away to allow visualization of the plunger head contacting the trigger fingers during an injection.

Once the safety device 100 and medicine cartridge subassembly 300, are assembled together the completed drug delivery safety device 400 (FIG. 9) is ready for its intended use by patients and or nurses. Prior to device 400 use an end user would first remove an industry standard needle shield 230 exposing the needle 220 (FIG. 10). The needle 220 could then be inserted into a patient and the plunger 140 depressed to propel the contents of the medicine cartridge 200 into the patient. As the plunger 140 is depressed it is guided and contained by trigger finger guards 115 located on the body component 110 at opposing ends of the syringe flange reference surface 131. The trigger finger guards 115, which have an elongate body having a arcuate profile, extend proximally beyond the trigger finger 121 and distally beyond the syringe flange reference surface 131. There are chamfer features 114 on the trigger finger guards 115 which help align and center the plunger head 142 into the device activation area 150 of the safety device 100 (FIG. 11-14). In order to properly activate the safety device 100, the plunger head 142 angled surface 143 must interface with the angled surface 122 of the trigger fingers 121 (FIGS. 15, 16, 17 and 18). In instances of prior art, no such plunger alignment features are present, which increases the risk of an unsuccessful device activation due to improper plunger-trigger mechanism surface interaction.

Figure 22:
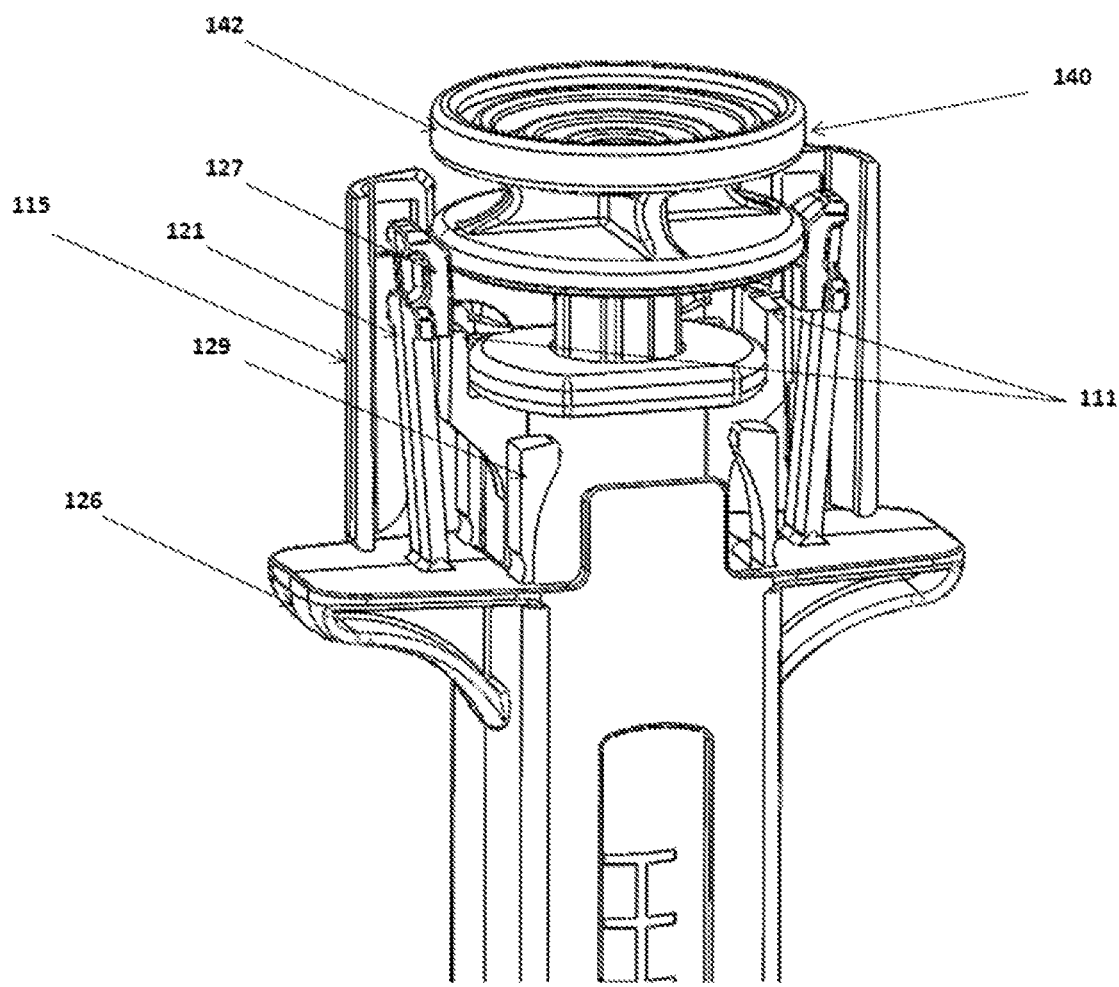
FIG. 22 is a partial isometric view of the safety device with a portion of the body cut away for visualization of the plunger head bending the trigger fingers off of the body seats.
Figure 23:
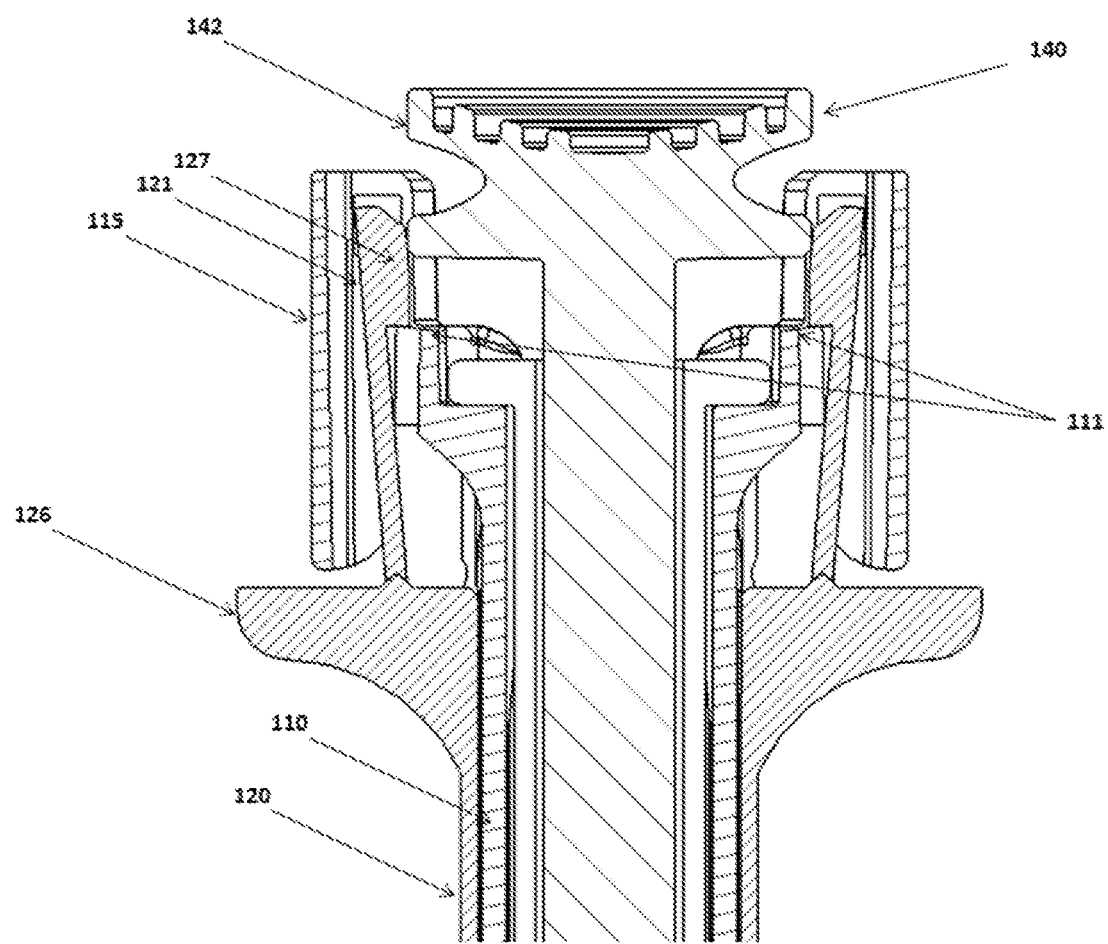
FIG. 23 is a partial cross sectional view of the safety device displaying the plunger head bending the trigger fingers off of the body seats.
Figure 24:
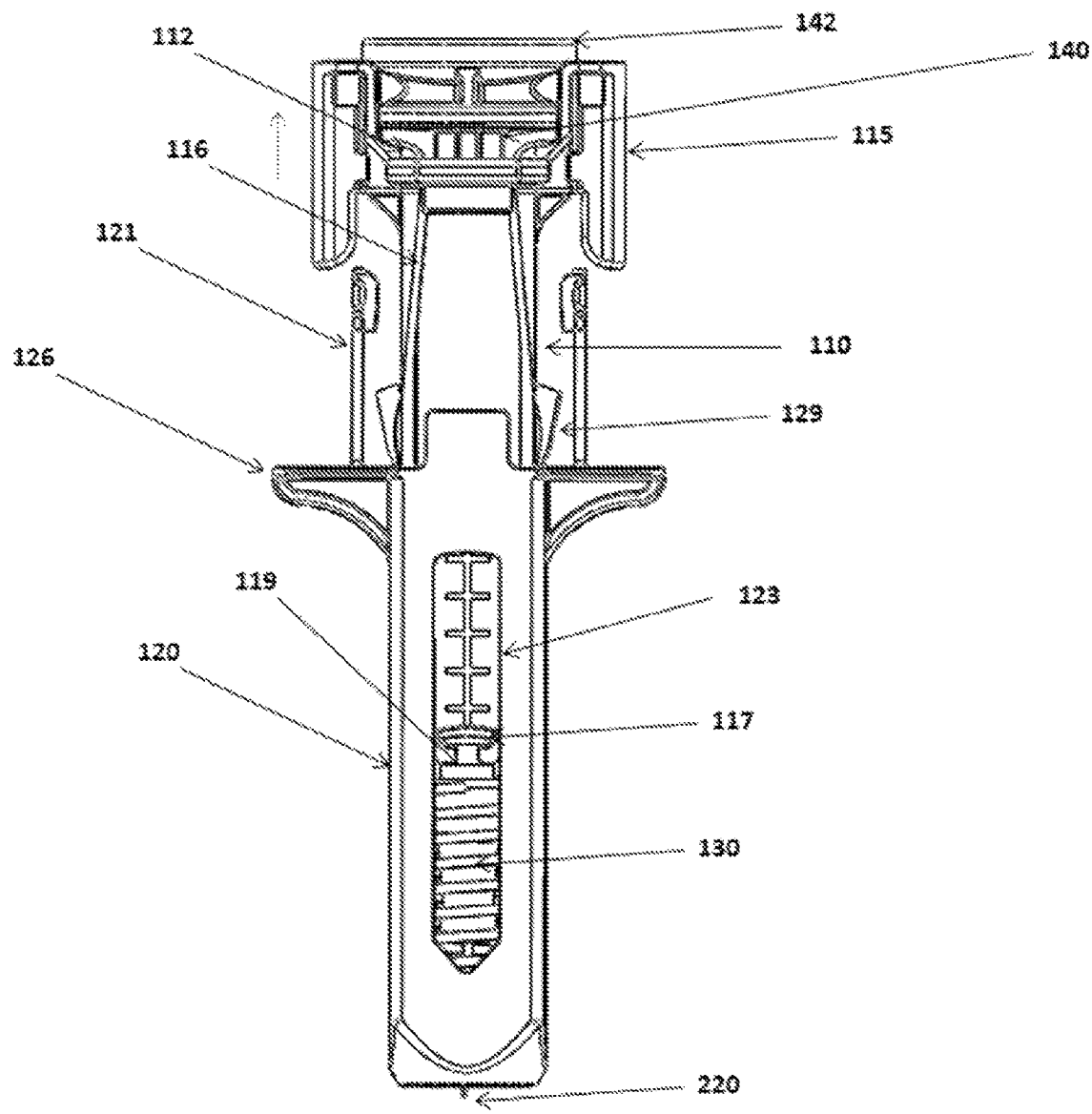
FIG. 24 is a front view of the safety device after an injection, where the trigger fingers have been pushed off the body seats and the spring is releasing its energy, causing the needle to be covered.
Figure 25:
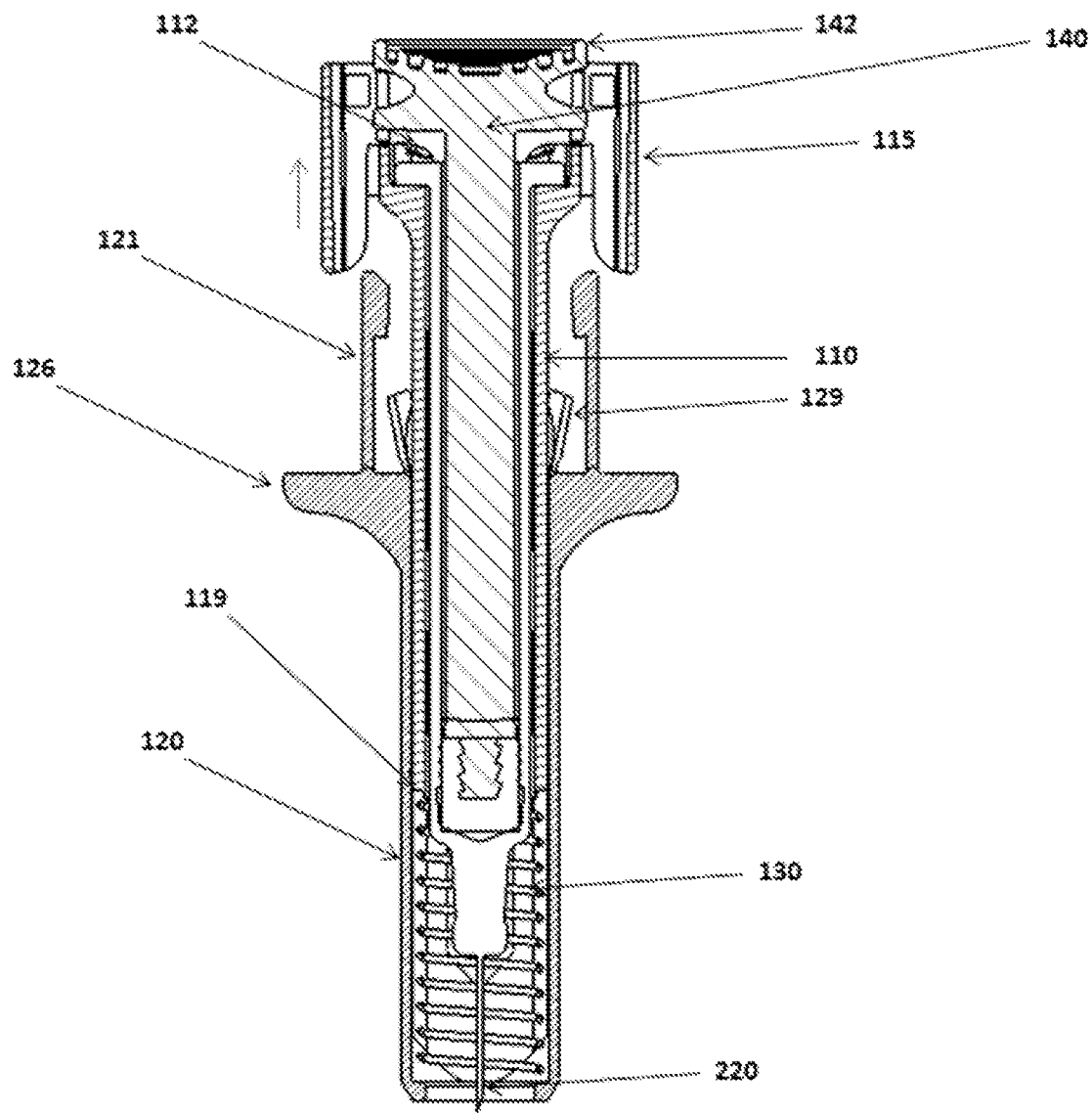
FIG. 25 is a cross sectional view of the safety device after an injection, where the trigger fingers have been pushed off the body seats and the spring is releasing its energy, causing the needle to be covered.
Figure 26:
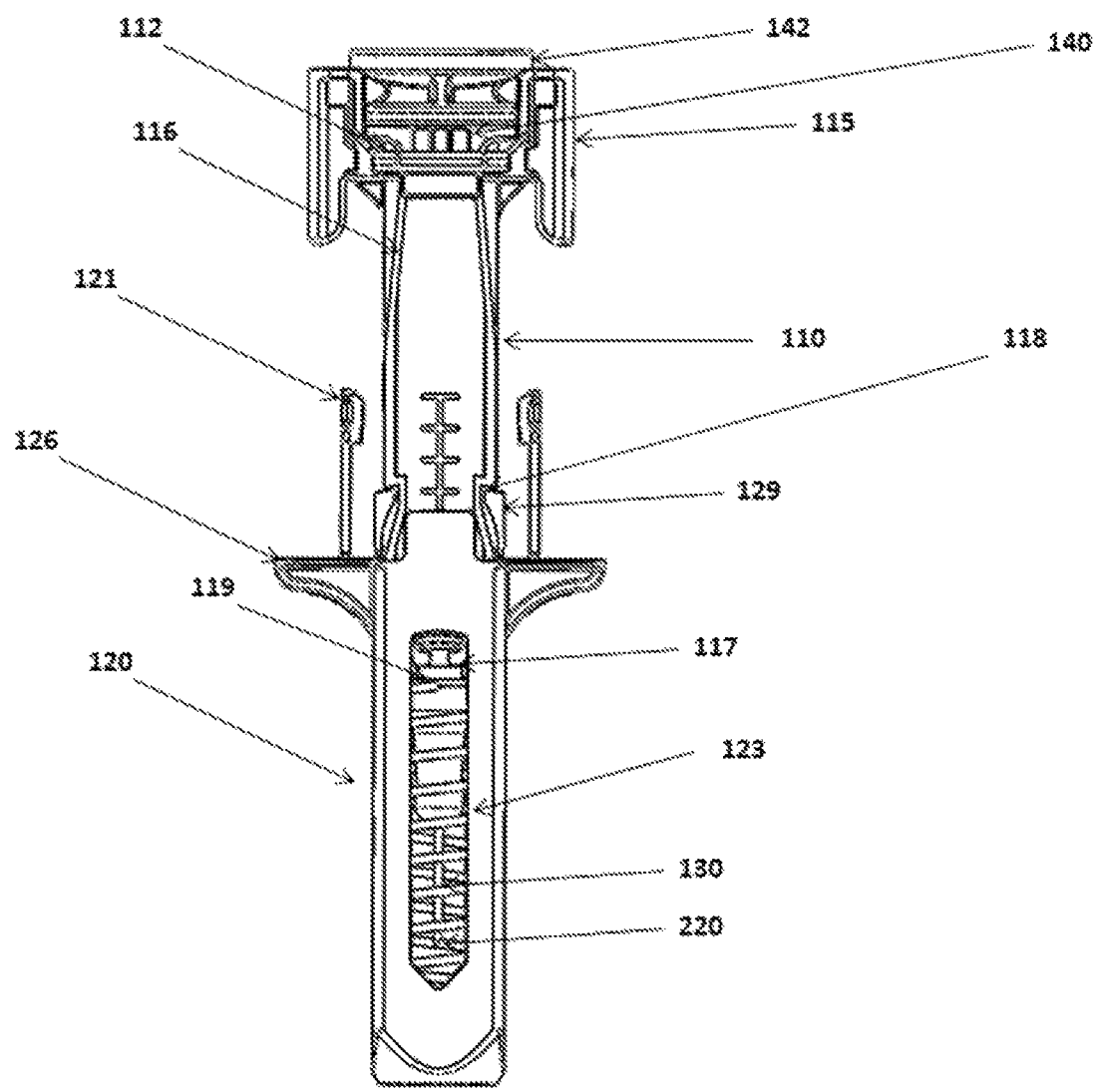
FIG. 26 is a front view of the safety device after an injection, and the device in a locked state.
Figure 27:
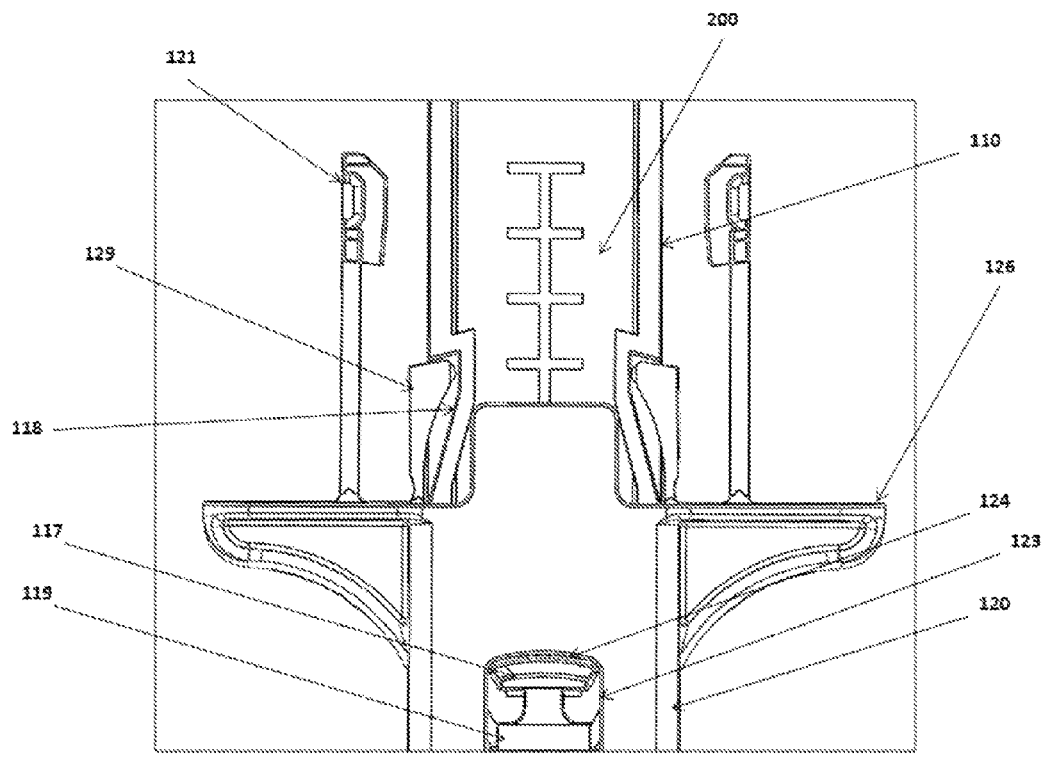
FIG. 27 is an enlarged partial front view of the safety device in a locked state after an injection.
Figure 28:
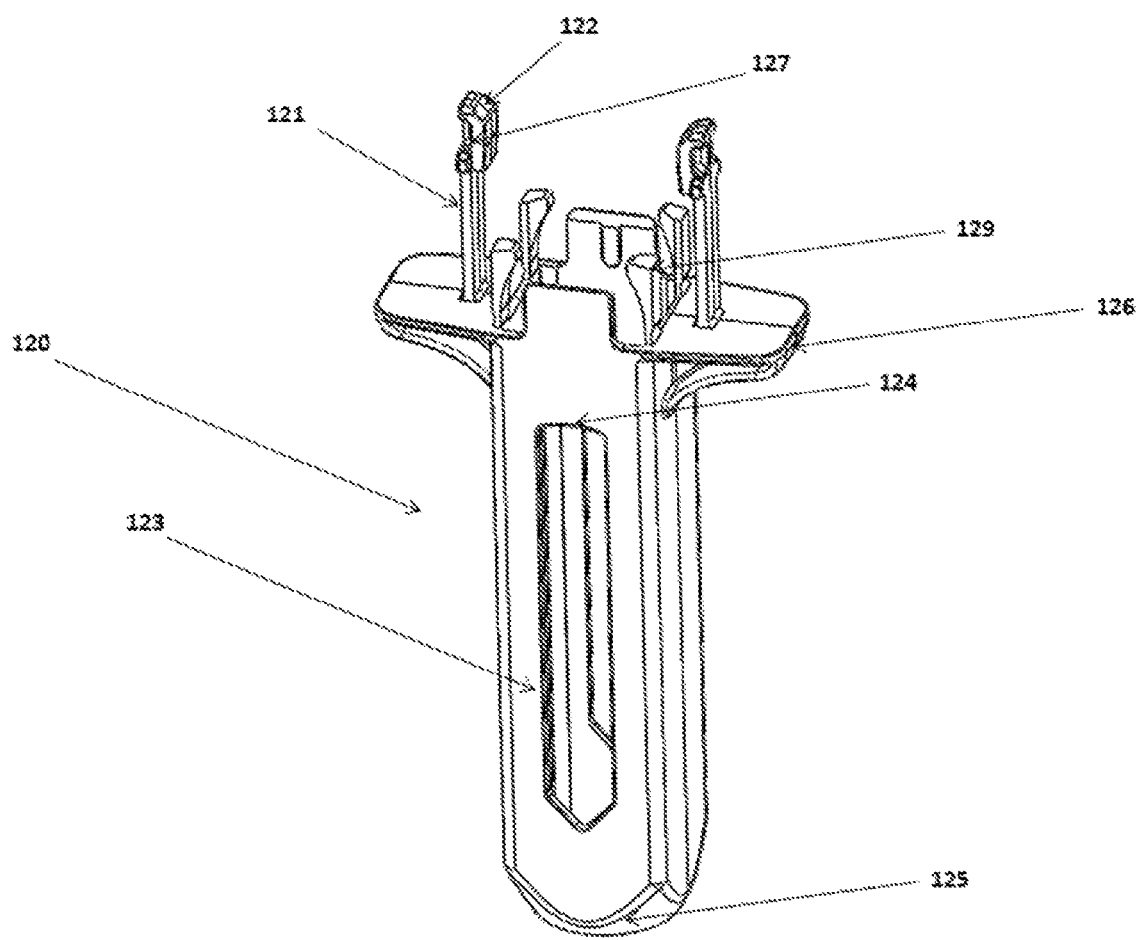
FIG. 28 is an isometric view of a guard of the safety device.
Figure 29:
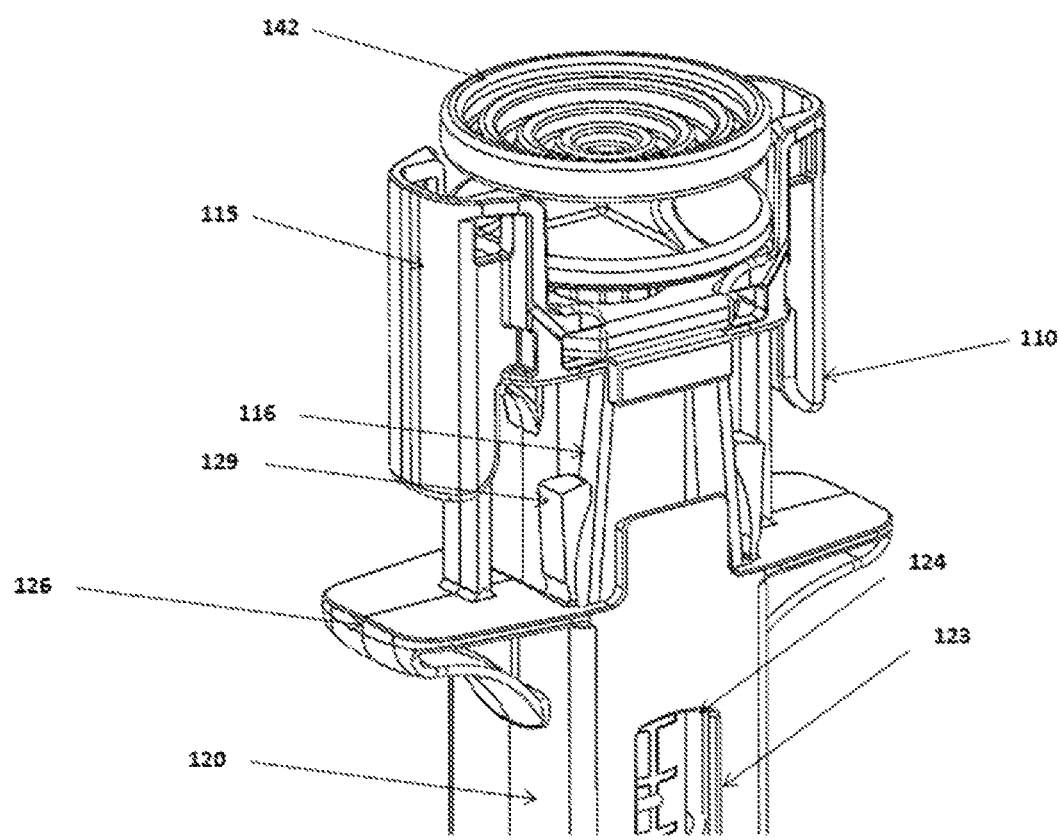
FIG. 29 is a partial isometric view of the safety device where the trigger fingers have been pushed off the body seats and the spring is releasing its energy, causing the needle to be covered, and the latch fingers to ride along the angular body surface.

Continued depression of the plunger 140 after surface contact between itself and the trigger fingers 121 cause the trigger fingers 121 to bend or flex outwardly, away from the center of the device (FIGS. 22 and 23). The trigger fingers 121, having been bent, lose contact with the trigger finger seats 111 on the body component 110, effectively de-coupling the guard 120 from the body 110. As a result, when the end user removes the needle 220 from the injection site the spring 130 is free to release its energy and extend. As the spring 130 extends it pushes the guard 120 relative to the body to extend the guard 120 over the needle 220. During the action of pushing the guard 120 over the needle 220, the body 110, which contains the medicine cartridge subassembly 300 within the syringe retention features 112, moves away or retracts proximally from the guard 120. Correspondingly, the distal end 119 of the body 110 moves within the guard toward the finger flanges 126 (FIGS. 24 and 25). During the initial displacement of the guard 120 relative to the body 110, the latch fingers 129 encounter an angled surface 116 on the body (FIG. 29). The angled surface 116 causes the latch fingers 129 to increasingly bend as they move down the angled surface 116. The relative movement between the body 110 and the guard 120, manifesting from the stored energy of the spring 130 is halted after sufficiently covering the needle 220 within the guard 120 (FIG. 26), by the stop tabs 117 which ride in a window 123 on the body 110 (FIG. 28). The stop tabs 117 encounter the top 124 of the window 123 (FIG. 27), which acts as a mechanical stop for the body 110. At the point where the stop tabs 117 encounter the top of the window 124, the latch fingers 129 reach a pocket 118 within the body 110 and resile to their original perpendicular position, placing them within the body pocket 118 (FIGS. 26 and 27). The safety device 400 is now in its locked state, meaning if a user pushed on the distal end 125 of the guard 120, the guard 120 would remain fixed, as the latch fingers 129 would bear that load against the body pockets 118, thus protecting a user from an accidental needle stick injury.

In an alternative embodiment, the latch fingers 129 and pockets 118 can be configured such that the latch fingers 129 also act as stop tabs. In a further alternative embodiment, the trigger fingers 121 may include a bump that is received in a mating groove formed in the trigger finger seats 111 on the body component 110 to provide tactile feedback as the plunger disengages the trigger fingers 121 from the trigger finger seats 111.

Figures 30A, 30B:
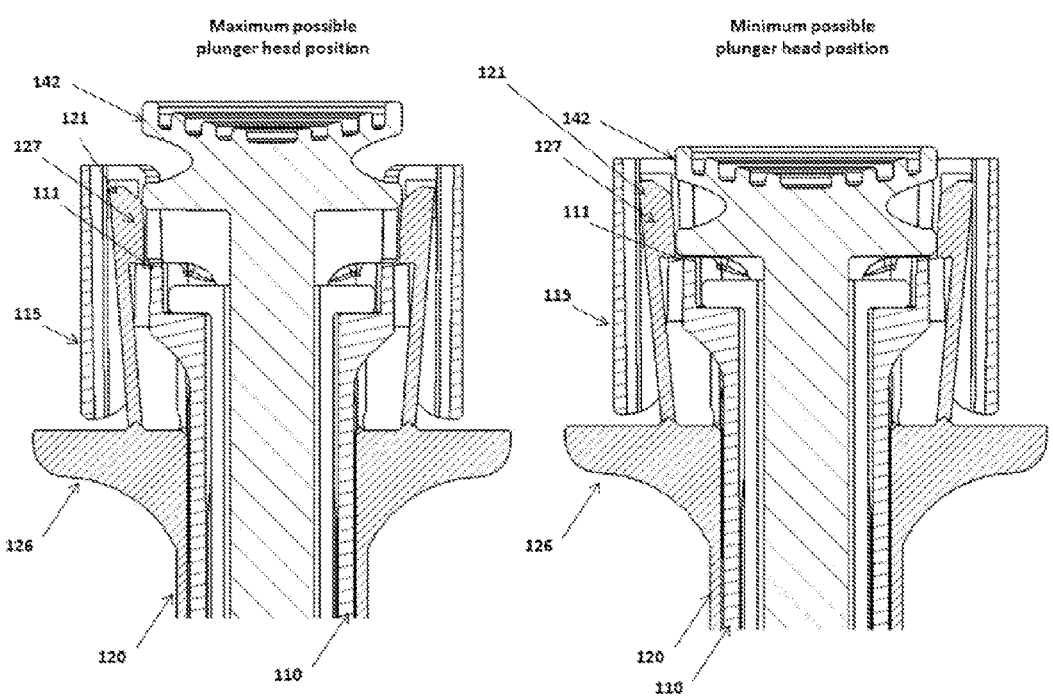
FIGS. 30A and B are cross sectional partial front views of the device showing the maximum and minimum plunger head positions due to syringe and syringe stopper tolerances.

In the manufacture of syringes and syringe plungers there can be significant tolerance ranges observed for certain dimensions. Several of these have an impact on the final vertical position of the plunger head 142 relative to the trigger fingers 121 (FIGS. 30A and 30B). Additionally, syringes and syringe plungers made by different manufacturers may have different tolerance ranges. In prior art, this variability in final plunger head position relative to the activation mechanism was accounted for by creating custom plunger lengths for a specific syringe and syringe plunger manufacturer combination. In the current design, a novel elongated trigger finger head 127 allows the device 100 to activate for all known syringe and syringe plunger tolerances (FIGS. 30A and 30B).

Figure 31:
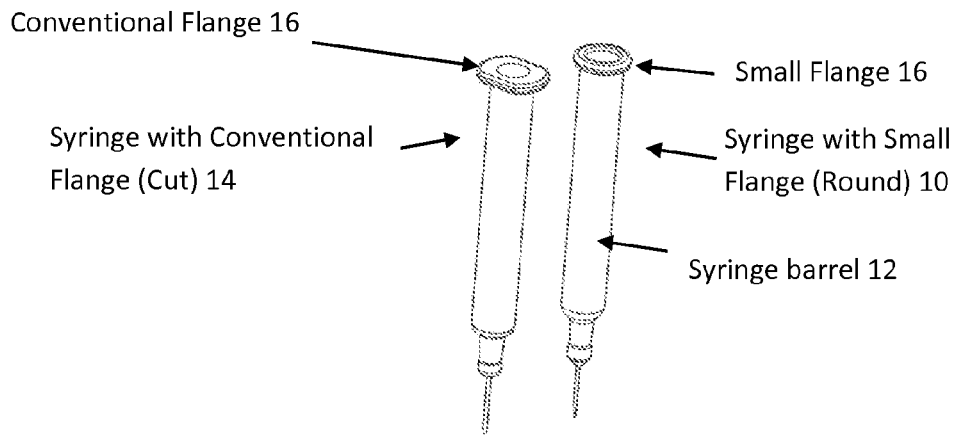
FIG. 31 is an isometric view providing a comparison of a syringe with a conventional flange in the cut state with a syringe having a small round flange.

In a further alternative, embodiments described herein are directed to an anti-needle stick safety device designed to be packaged around a medicine cartridge such as a glass syringe with a small round flange. A syringe 14 having a conventional flange 15 of the cut variety is shown in FIG. 31 alongside a syringe 10 having a small round (uncut) flange 16. The primary difference between the two flanges 15 and 16 is that the small flange 16 has a smaller outside diameter than the conventional flange 15. As shown, the small flange 16 has an outside diameter that approximates but is slightly larger than the outside diameter of a barrel 12 of the syringe 10.

Figure 32:
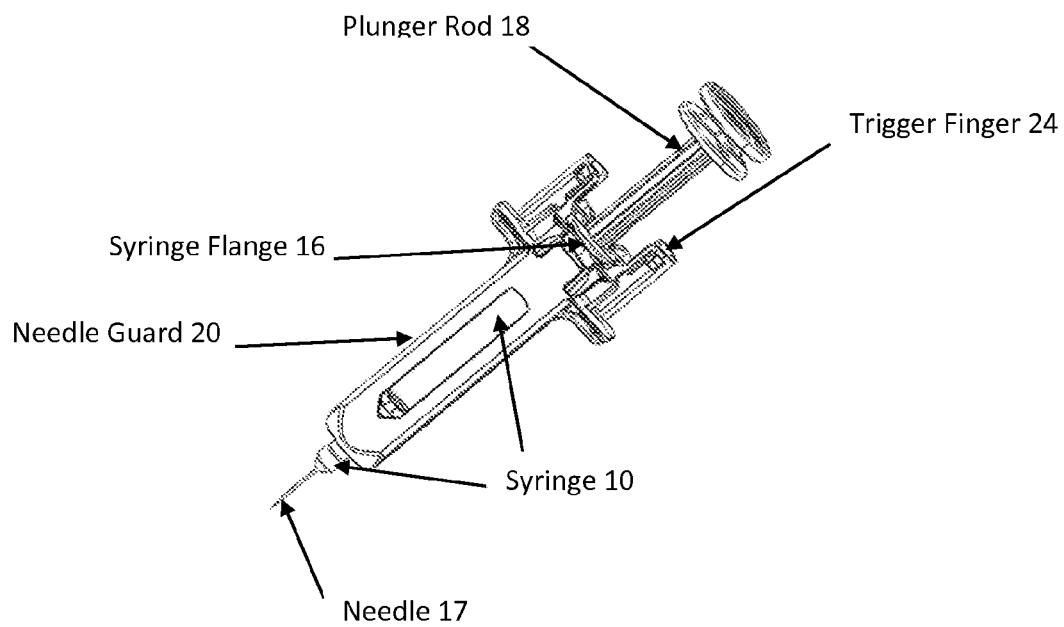
FIG. 32 is an isometric view showing a syringe having a small round flange with a safety device ready for injection.
Figure 33:
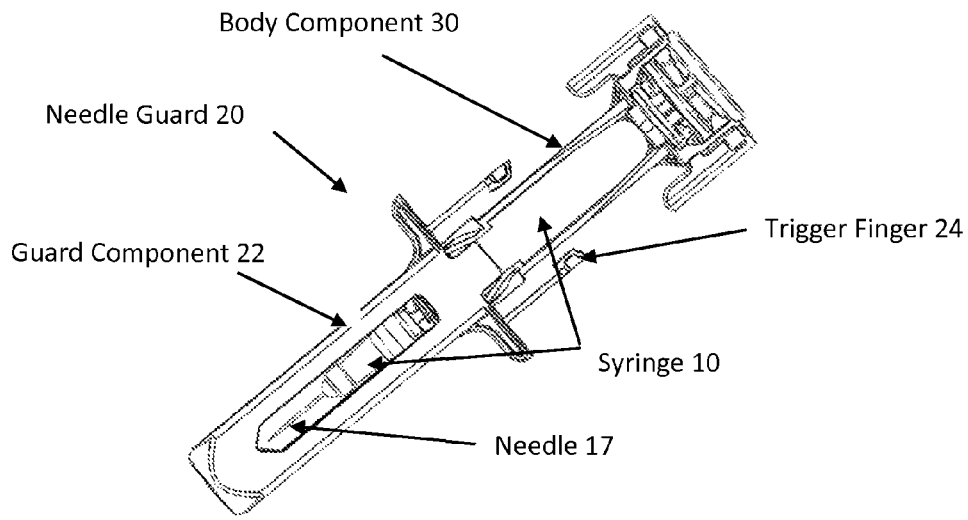
FIG. 33 is an isometric view showing a syringe having a small round flange with a safety device in the protected mode.

A safety device 20, i.e., a needle guard device, is shown in FIG. 32 assembled with a syringe 10 and shown in a configuration ready for injection. When the needle 17 is inserted into the target tissue and a plunger rod 18 is depressed to inject the medication from within a barrel 12 of the syringe 10, a safety mechanism 24 (see FIG. 33), i.e., trigger fingers, is triggered that releases a spring, forcing a body component 30, which holds the syringe 10, to move proximally with respect to a guard component 22. At the end of this proximal movement, the guard component 22 locks into position with respect to the body component 30 forming a protective shield around the used needle 17 and thereby preventing accidental needle stick injuries (see FIG. 33).

Figure 34:
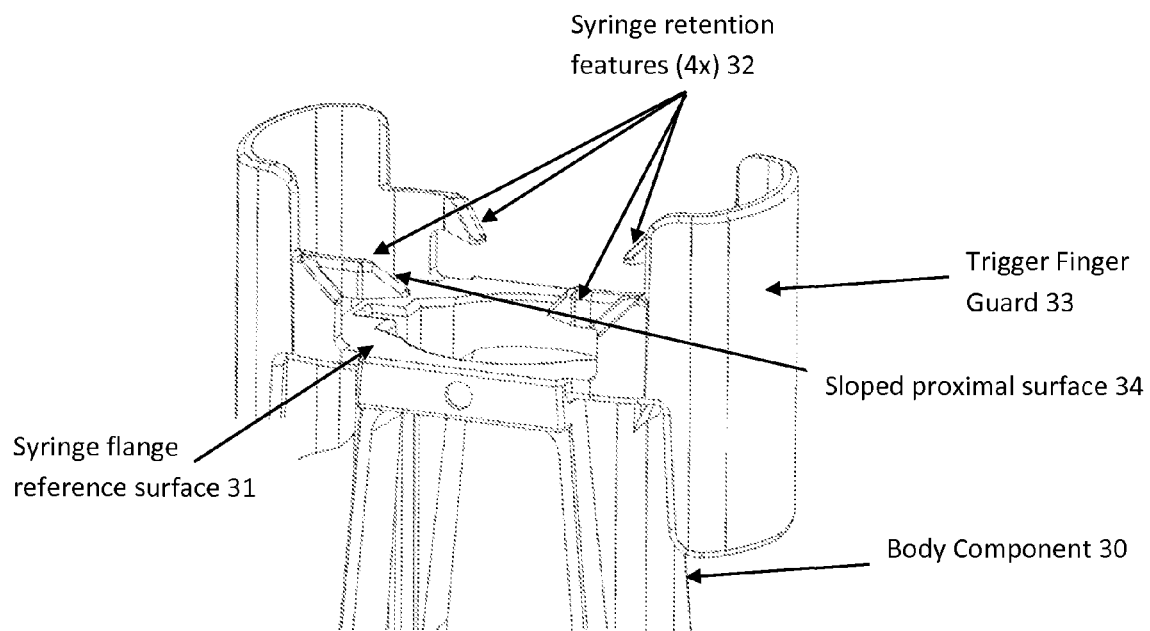
FIG. 34 is a partial side isometric view of a body component of the safety device showing the syringe retention features.
Figure 35:
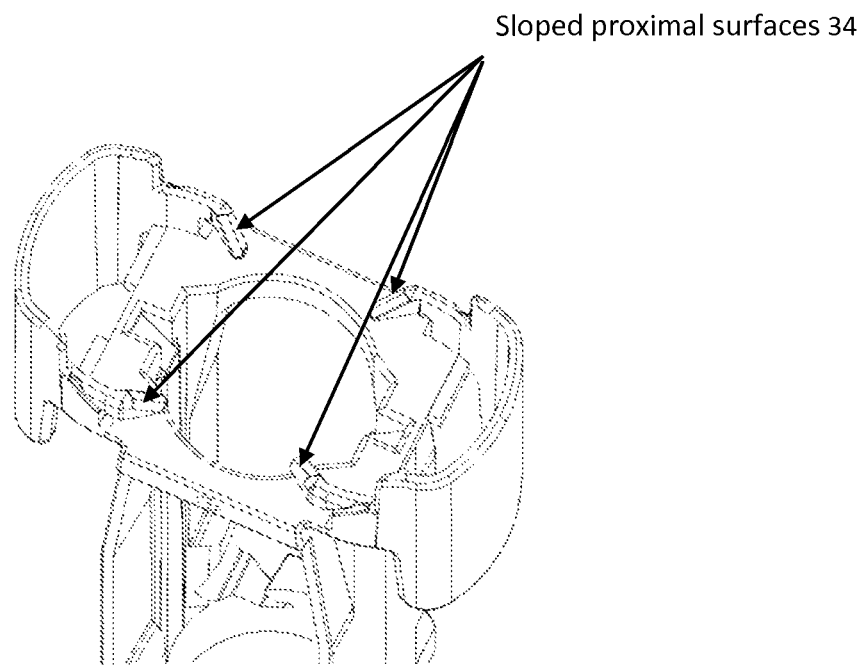
FIG. 35 is a partial oblique isometric view of the body component of the safety device showing the syringe retention features.
Figure 36:
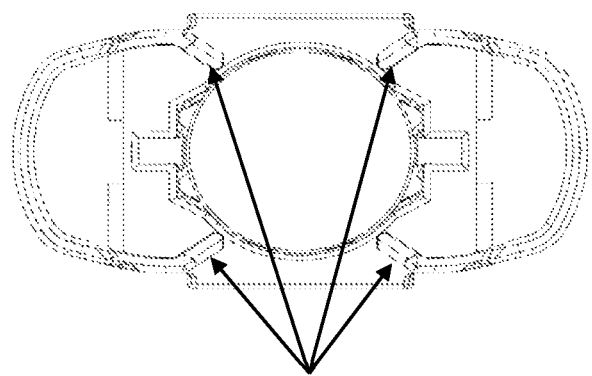
FIG. 36 is a proximal end view of the body component of the safety device showing the syringe retention features.
Figure 37:
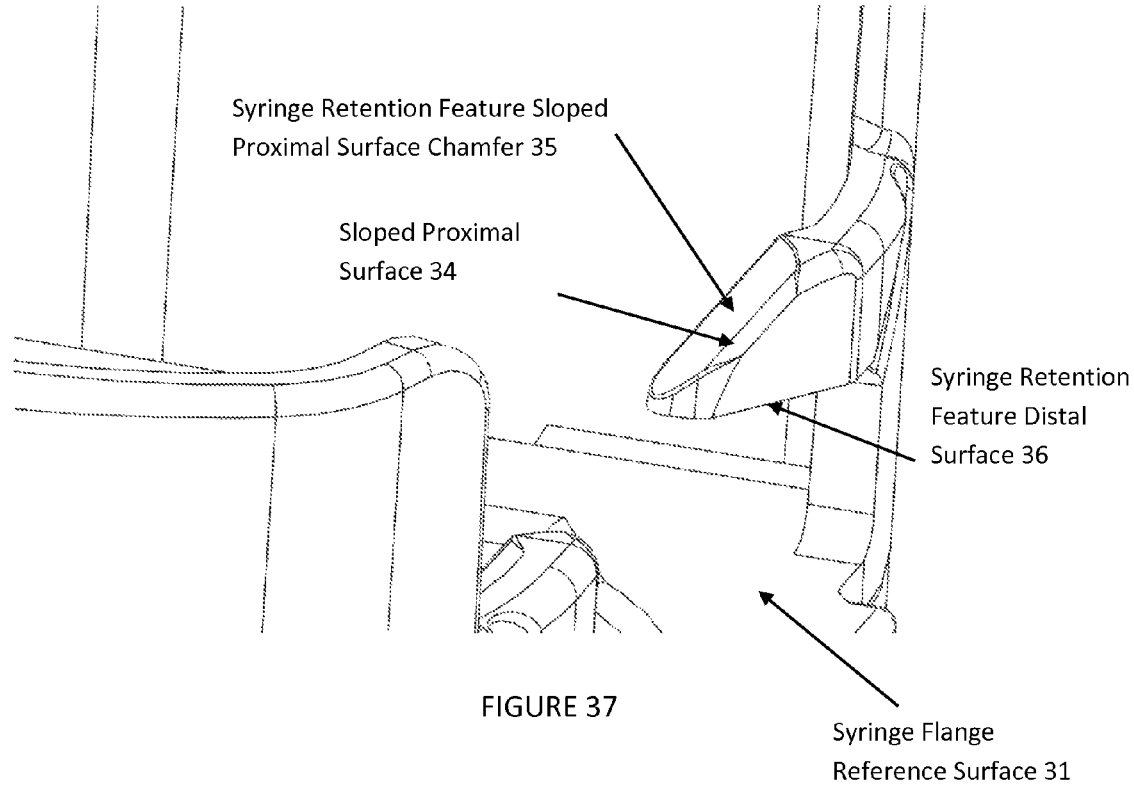
FIG. 37 is a detail isometric view of the body component of the safety device showing a syringe retention feature.
Figure 38:
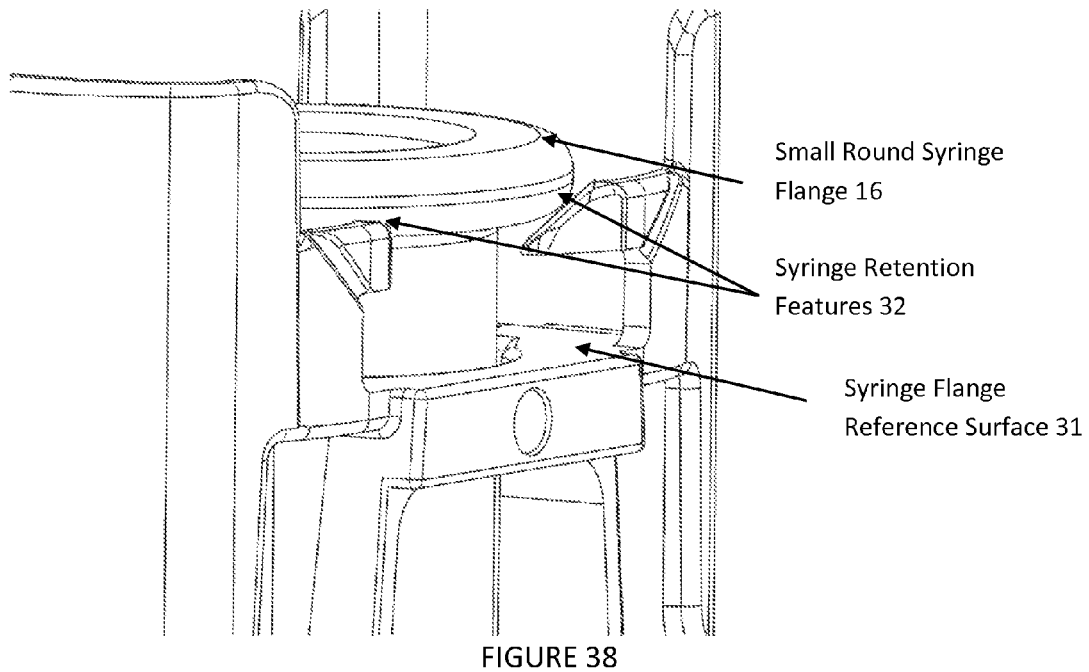
FIG. 38 is a detail isometric view showing the syringe flange abutting the retention feature sloped proximal surface chamfer during the assembly process.

An example of syringe flange retention features 32 on the body component 30 of the type illustrated in FIGS. 2 and 3 is shown in greater detail in FIG. 34. A syringe flange reference surface 31 is also shown. The syringe flange 16 arrests against the reference surface 31 after insertion into the safety device 20. The flexible retention features 32 have angled surfaces 34 against which the syringe flange 16 centers itself during insertion. The retention features 32 are angled toward the near-center of the safety device 20, as shown in FIGS. 35 and 36, so that as the syringe 10 is forced against the syringe retention features 32 during assembly, there is a lateral force on the retention features 32 pushing them away from the center of the safety device 20 and, with increasing insertion force and travel, deflecting them enough to allow the flange 16 to pass by. In addition, the sloped proximal surfaces 34 of the syringe retention features 32 have chamfers 35 (see FIG. 37) that are further sloped toward the center of the safety device 20 such that the syringe flange 16 (see FIG. 38) is able to exert more of a laterally directed force than if the sloped surfaces 34 didn't include the chamfers 35. This allows the syringe retention features 32 to be positioned as close to the syringe barrel 12 as possible so that after the syringe 10 is inserted, the syringe retention features 32 recoil back to a position that provides maximum interference with the syringe flange 16. If the syringe retention features 32 were initially positioned further towards the center of the safety device 20 than where they would initially contact the outer wall of the syringe barrel 12, then they would scrape and possibly damage the syringe label during insertion. Hence it is necessary to have the syringe retention features 32 positioned as close to the syringe barrel 12 as possible in order to provide maximum holding force against the flange 16 of an installed syringe 10.

Figure 39:
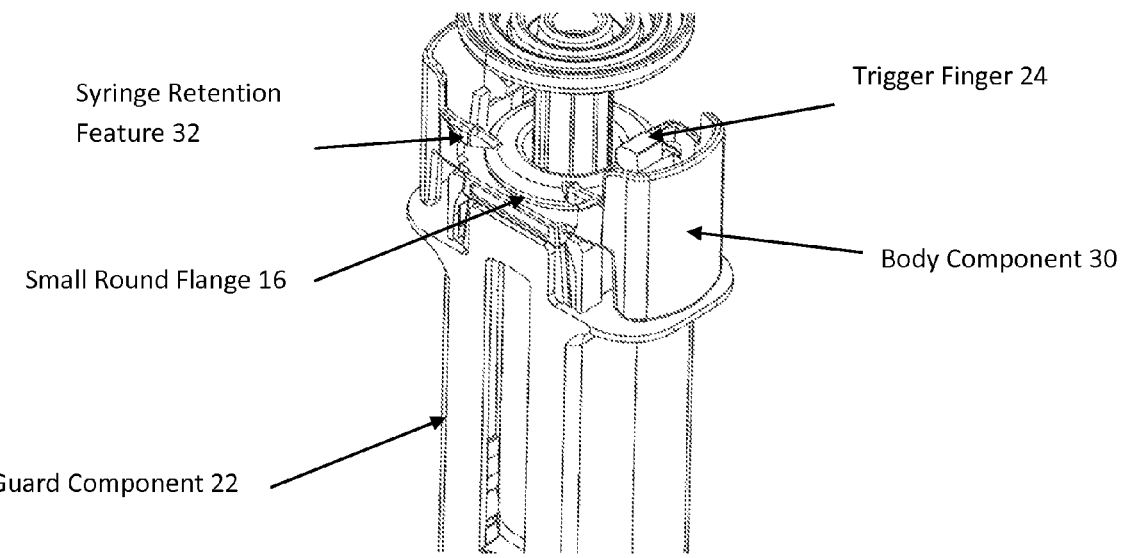
FIG. 39 is a partial side isometric view showing the syringe having the small round flange installed into the safety device.

After installation into the safety device 20, the syringe 10 is held in place by an interaction between the distal surface 36 of the syringe retention features 32 (see FIGS. 37 and 39), the syringe flange 16, and the syringe flange reference surface 31 of the safety device 20. As such, the distal surface 36 of the syringe retention features 32 are without sloped surfaces or flanges to maximize the holding strength of the retention features 32 against the syringe flange 16 during proximally directed forces on the syringe 10.

Figure 40:
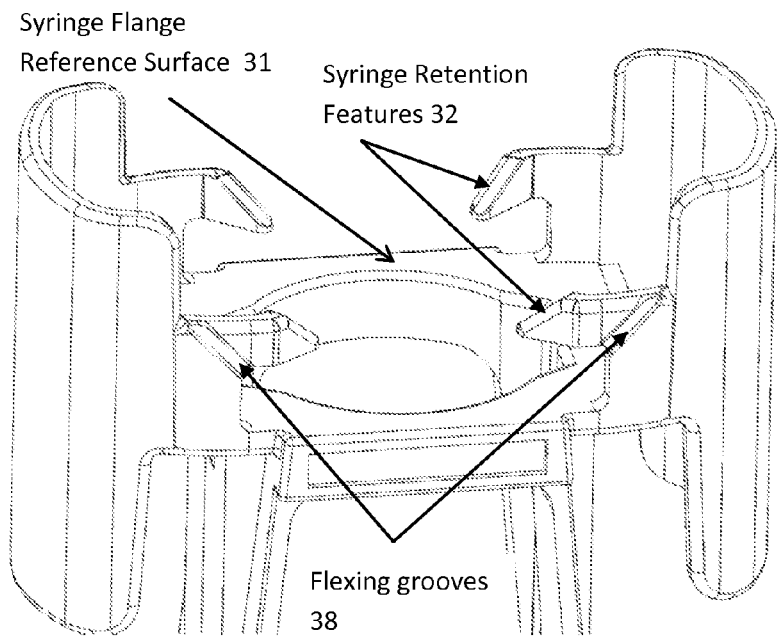
FIG. 40 is a detail isometric view of the body component of the safety device showing a syringe retention feature with flexing hinges.

To reduce the forces on the syringe flange 16 during installation into the safety device 20, it is advantageous to have the syringe retention features 32 flex laterally with low force but to provide high rigidity when deflected proximally to better resist proximally directed motion of the syringe 10. FIG. 40 shows an alternative embodiment that accomplishes this by employing a flexing groove 38 in the lateral side of the syringe retention features 32. The flexing grooves 38 are oriented substantially perpendicular to the direction of lateral deflection so that they may act as a hinge for the retention features 32 in the lateral direction, but at the same time providing rigidity to the retention features 32 in the distal, or more importantly, the proximal direction. The grooves 38 may also be angled as shown in FIG. 40, allowing the retention features 32 to flex proximally slightly (or less distally) during the initial lateral deflection to compensate for any distal deflection that they may experience as the syringe flange 16 is pushed proximally past them. If the retention features 32 were to flex too much distally, they might then occupy the space that was meant for the syringe flange 16 once it had reached the syringe reference surface 31, preventing the syringe 10 from being fully installed or captured by the retention features 32.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, unless otherwise stated, and the invention can be performed using different or additional process actions, or a different combination or ordering of process actions. As another example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A needle guard safety device couplable to a ready-to-fill syringe comprising
    a body for receiving a medicine cartridge, the medicine cartridge having a medicine cartridge body and a medicine cartridge flange extending outwardly from a proximal end of the medicine cartridge body,
    a needle guard moveable relative to the body for covering a needle extending from the medicine cartridge,
    a plunger to dispense medicine from the medicine cartridge, and
    a spring for activation of the needle guard to cover the needle,
    wherein trigger fingers of the needle guard are seated on the body retaining the needle guard in a pre-activation position where the needle is exposed and spaced such that the medicine cartridge flange will not unseat the trigger fingers during assembly of the medicine cartridge into the body.

2. The needle guard safety device of claim 1, wherein the trigger fingers of the needle guard are spaced such that the medicine cartridge flange minimally contacts the trigger fingers during assembly without unseating the trigger fingers during assembly.

3. The needle guard safety device of claim 1, further comprising syringe capture features on the body, wherein the capture features include an angled surface that interfaces with the medicine cartridge flange during insertion requiring a normal force for assembly.

4. The needle guard safety device of claim 1, wherein the spring comprising end coils at first and second ends of the spring and inner coils extending between the end coils, wherein the end coils are larger in diameter compared with the inner coils of the spring reducing the likelihood of the end coils interfering with the medicine cartridge.

5. The needle guard safety device of claim 1, further comprising elongated trigger finger heads to allow activation of the needle guard for all known syringe and syringe plunger tolerances.

6. A needle guard safety device couplable to a syringe comprising
    a body for receiving a syringe, the syringe having a syringe body and a flange extending outwardly from the syringe body,
    a guard moveable relative to the body for covering a needle extending from the syringe body, the guard including trigger fingers seated on the body retaining the guard in a pre-activation position where the needle is exposed,
    a plunger to dispense medicine from the syringe, and
    a spring for activation of the guard to cover the needle, and
    syringe capture features on the body, wherein the syringe capture features include an angled surface directed toward a center of the body and that interfaces with the flange during insertion of the syringe into the body.

7. The needle guard safety device of claim 6, wherein the capture features include a groove.

8. The needle guard safety device of claim 6, wherein the angled surface of the capture features include a chamfered surface angled toward the center of the body.

9. The needle guard safety device of claim 7, wherein the groove is angled to provide deflection of the capture features in lateral and proximal directions.

10. The needle guard safety device of claim 7, wherein the groove is configured to reduce deflection of the capture features in distal direction as the capture feature deflects in the lateral direction.

11. The needle guard safety device of claim 6, wherein the capture features are configured to capture a small round flange of the syringe.

12. The needle guard safety device of claim 6, wherein the angled surface of the capture features is configured to cause the capture features to be deflected laterally.

13. The needle guard safety device of claim 8, wherein the chamfered surface of the capture features is configured to cause the capture features to be deflected laterally.

14. The needle guard safety device of claim 11, wherein the small round flange of the syringe has an outside diameter that approximates and is larger than the outside diameter of a barrel of the syringe.

15. An anti-needle stick safety system comprising,
    a syringe having a barrel, a flange formed on the proximal end of the barrel, and a needle coupled to the distal end of the barrel,
    an anti-needle stick device comprising
    a body for receiving the syringe,
    a guard moveable relative to the body for covering the needle, the guard including trigger fingers seated on the body retaining the guard in a pre-activation position where the needle is exposed,
    a plunger to dispense medicine from the syringe, and
    a spring for activation of the guard, and
    syringe capture features on the body, wherein the capture features include an angled surface directed toward a center of the body and that interfaces with the flange during insertion of the syringe into the body.

16. The needle guard safety device of claim 15, wherein the capture features include a groove.

17. The needle guard safety device of claim 15, wherein the angled surface of the capture features include a chamfered surface angled toward the center of the body.

18. The needle guard safety device of claim 16, wherein the groove is angled to provide deflection of the capture features in lateral and proximal directions.

19. The needle guard safety device of claim 16, wherein the groove is configured to reduce deflection of the capture features in distal direction as the capture feature deflects in the lateral direction.

20. The needle guard safety device of claim 15, wherein the flange of the syringe is a small round flange and wherein the capture features are configured to capture the small round flange of the syringe.

21. The needle guard safety device of claim 15, wherein the angled surface of the capture features is configured to cause the capture features to be deflected laterally.

22. The needle guard safety device of claim 17, wherein the chamfered surface of the capture features is configured to cause the capture features to be deflected laterally.

23. The needle guard safety device of claim 20, wherein the small round flange of the syringe has an outside diameter that approximates and is larger than the outside diameter of a barrel of the syringe.

* * * * *